US009603799B2

(12) United States Patent
Sorayya et al.

(10) Patent No.: US 9,603,799 B2
(45) Date of Patent: Mar. 28, 2017

(54) LIPOSOMAL VACCINE ADJUVANTS AND METHODS OF MAKING AND USING SAME

(71) Applicant: HTD Biosystems Inc., Pleasanton, CA (US)

(72) Inventors: Aryo Sorayya, Danville, CA (US); Mitra Mosharraf, Danville, CA (US); Rajiv Nayar, Danville, CA (US)

( * ) Notice: Subject to any disclaimer, the term of this patent is extended or adjusted under 35 U.S.C. 154(b) by 0 days.

(21) Appl. No.: 14/216,605

(22) Filed: Mar. 17, 2014

(65) Prior Publication Data
US 2014/0341974 A1 Nov. 20, 2014

Related U.S. Application Data

(63) Continuation-in-part of application No. 13/837,637, filed on Mar. 15, 2013, now abandoned.

(51) Int. Cl.
A61K 9/127 (2006.01)
A61K 39/08 (2006.01)
A61K 9/00 (2006.01)
A61K 39/00 (2006.01)
A61K 47/24 (2006.01)
A61K 39/39 (2006.01)

(52) U.S. Cl.
CPC ............ *A61K 9/127* (2013.01); *A61K 9/0019* (2013.01); *A61K 39/0005* (2013.01); *A61K 39/08* (2013.01); *A61K 39/39* (2013.01); *A61K 47/24* (2013.01); *A61K 2039/545* (2013.01); *A61K 2039/55555* (2013.01)

(58) Field of Classification Search
CPC .. A61K 2300/00; A61K 39/39; A61K 9/0019; A61K 9/127; A61K 2039/55511; A61K 2039/55555; A61K 39/12; A61K 9/1075; A61K 9/19; A61K 9/51; A61K 31/00
See application file for complete search history.

(56) References Cited

U.S. PATENT DOCUMENTS

| | | | |
|---|---|---|---|
| 5,290,563 A | 3/1994 | Millet-Genin et al. | |
| 6,045,828 A * | 4/2000 | Bystrom | A61K 9/0075 424/404 |
| 2005/0142114 A1 | 6/2005 | Gieseler et al. | |
| 2008/0089927 A1* | 4/2008 | Malinin | 424/450 |
| 2008/0145413 A1 | 6/2008 | Panzner et al. | |
| 2008/0268028 A1 | 10/2008 | Zurbriggen et al. | |
| 2010/0233251 A1 | 9/2010 | Andrian et al. | |
| 2011/0002983 A1 | 1/2011 | Hipler et al. | |
| 2011/0092739 A1 | 4/2011 | Chen et al. | |
| 2012/0015865 A1 | 1/2012 | Zelphati et al. | |
| 2013/0177629 A1 | 7/2013 | Martin et al. | |
| 2013/0287857 A1 | 10/2013 | von Andrian et al. | |
| 2013/0323298 A1 | 12/2013 | Goodwin et al. | |
| 2014/0017279 A1 | 1/2014 | Brito et al. | |
| 2014/0079774 A1 | 3/2014 | Brinker et al. | |

FOREIGN PATENT DOCUMENTS

WO  WO 9515762 A1 * 6/1995

OTHER PUBLICATIONS

Watson DS, Endsley AN, Huang L. Design considerations for liposomal vaccines: influence of formulation parameters on antibody and cell-mediated immune responses to liposome associated antigens. Vaccine. Mar. 16, 2012;30(13):2256-72. doi: 10.1016/j.vaccine.2012.01.070. Epub Feb. 2, 2012. Review. Erratum in: Vaccine. Aug. 24, 2012;30(39):5799.*
Lutwyche P, Cordeiro C, Wiseman DJ, St-Louis M, Uh M, Hope MJ, Webb MS, Finlay BB. Intracellular delivery and antibacterial activity of gentamicin encapsulated in pH-sensitive liposomes. Antimicrob Agents Chemother. Oct. 1998;42(10):2511-20.*
Ewert KK, Ahmad A, Bouxsein NF, Evans HM, Safinya CR. Non-viral gene delivery with cationic liposome-DNA complexes. Methods Mol Biol. 2008;433:159-75.*
Sorayya, A. "Designing a Novel Freeze-Stable Tetanus Vaccine." Intel International Science and Engineering Fair (Intel ISEF), 2013.
Fraga et al. Influence of phospholipid composition on cationic emulsions/DNA complexes: physiochemical properties, cytotoxicity, and transfection on Hep G2 cells. Int J Nanomedicine (2011) 6:2213-20. Epub Oct. 7, 2011.
Chen et al. "An overview of liposome lyophilization and its future potential." J Control Release (2010) 142:299-311. Epub Oct. 27, 2009.
O'Hagan, DT. Recent advances in immunological adjuvants: the development of particulate antigen delivery systems. Expert Opin Investig Drugs. (1998) 7(3):349-59.
Sorayya, A. (2012) Contra Costa County Science & Engineering Fair. "Development of a lyophilizable vaccine for delivering a model protein antigen." 1st Place. (Also presented at CA State Science Fair where same presentation won "Project of the Year" in 2012).
Sorayya A. "Overcoming the Cold Chain: Designing a Novel Freeze-Stable Vaccine." CA State Fair Project 2012 Project Summary. Apr. 30, 2012.
Sorayya et al. Designing a novel freeze-stable vaccine as an alternative to aluminum-based vaccines. Abstract. 2012 AAPA Annual Meeting and Exposition Oct. 14-17, 2012.
Nayar and Mosharraf. (2010) "Effective approaches to formulation development and biopharmaceuticals, in Formulation and Process Development Strategies for Manufacturing Biopharmaceuticals" (eds F. Jameel and S. Hershenson), John Wiley & Sons, Inc. Hoboken, NJ USA.
Altin and Parish. (2006) "Liposomal vaccines—targeting the delivery of antigen." Methods 40:39-52.

(Continued)

Primary Examiner — Rachel B Gill
(74) Attorney, Agent, or Firm — Lewis Kohn & Walker LLP; David M. Kohn; Kari Moyer-Henry

(57) ABSTRACT

A vaccine adjuvant composition comprising: a lipid selected from the group consisting of: dipalmitoyl phosphatidlcholine (DPPC), dipalmitoyl phosphatidylglycerol (DPPG), dioleoyl phosphatidylcholine (DOPC), and cholesterol and containing a positively or negatively charged lipid with associated/entrapped protein antigen.

7 Claims, 28 Drawing Sheets

(56) References Cited

OTHER PUBLICATIONS

Gregoriadis et al. (1999) "Vaccine Entrapment in Liposomes." Methods 19:156-162.

Milicic et al. (2012) Small Cationic DDA:TBD Liposomes as Protein Vaccine Ajvants Obviate the Need for TLR Agonists in Inducing Cellular and Humoral Responses. PLoS One 7(3): e34255. doi:10.1371/journal.pone.0034255.

Mishra et al. (2007) "Liposomes as adjuvant for combination vaccines." Indian Journal of Experimental Biology 45:237-241.

* cited by examiner

LIPOSOMAL VACCINE ADJUVANTS AND METHODS OF MAKING AND USING SAME

CROSS REFERENCE TO RELATED APPLICATIONS

This application is a continuation-in-part of U.S. patent application Ser. No. 13/837,637, filed Mar. 15, 2013, the contents of which are incorporated by reference herein.

FIELD OF THE INVENTION

This application relates generally to the field of vaccine compositions and methods of making or using same. Specifically, this application relates to liposomal vaccine compositions for use in promoting a specific immune response, and methods of processing such compositions in a manner which promotes degrees of protection of the composition from external environmental factors.

BACKGROUND OF THE INVENTION

The majority of vaccines currently in development belong to a specific class of subunit vaccine compositions, which consist of recombinant or purified pathogen-specific proteins or encoded antigens (from DNA) that will be expressed and presented in vivo in order to accomplish or elicit the desired immunogenic response. This type of vaccine presents an antigen to the immune system without introducing viral particles, whole or otherwise. While evidence suggests that live, attenuated pathogens and viral vectors can induce protective effects, they often cause unwanted side effects or raise safety concerns, which is one reason why subunit vaccines have risen to prominence in the field (Arvin et al., "New viral vaccines", *Virology*, 344:240-249 (2006); Yang et al., "A novel peptide isolated from phage library to substitute a complex system for a vaccine against staphylococci infection", *Vaccine*, 24:1117-1123 (2006))

One weakness of this technique is that isolated proteins can be denatured and thus will be associated with antibodies that are distinct from the desired antibodies. Another method of making subunit vaccine involves extracting an antigen's gene from the targeted virus (or bacterium) and inserting this gene into another virus or attenuated bacterium to make a recombinant virus or bacteria.

Researchers have also inserted an antigen's gene derived from a targeted virus into yeast. Examples of such resultant vaccines are well known in the art, including subunit viral vaccines derived from hepatitis B surface antigen (HBsAG) produced in yeast cells (Recombivax HB from Merck).

Such subunit vaccines, when administered alone, have relatively low efficacy for immune system activation, generally exhibiting poor immunogenicity (Toes et al., "Peptide vaccination can lead to enhanced tumor growth through specific T-cell tolerance induction", *Proc. Natl. Acad. Sci.*, 93:7855-7860 (1996)) and thus require the addition of adjuvants in order to elicit the appropriate level of immune system response to a particular antigen, initially through the innate, then subsequently the adaptive immune system (Grasso, P et al., *Essentials of Pathology for Toxicologists*, CRC Press (2002)).

Preferably, the adjuvant should be able to improve or facilitate antigen uptake by antigen presenting cells (APCs) and, ideally, then induce an Ag-specific immune response while simultaneously eliciting minimal toxicity to the individual.

Currently, aluminum-based adjuvants, such as aluminum phosphate and aluminum hydroxide, dominate their field and, prior to 2009, were the only licensed adjuvants in the U.S. Unfortunately, while the use of adjuvants such as alum and MF59 (oil-in-water, proprietary adjuvant owned by Novartis) can augment certain response to specific Ags, such agents can sometimes lead to induction of undesired, inappropriate responses (ie. generation of a humoral response rather than a cell mediated response) (Roberts et al., "Phase 2 study of the g209-2M melanoma peptide vaccine and low-dose interleukin-2 in advanced melanoma", *J. Immunother.*, 29(1):95-101 (2006)).

Additionally, these inorganic adjuvants face numerous other problems as they are frost sensitive and not readily lyophilizable. The limitations placed on vaccines by adjuvants that are not freeze-compatible severely restrict the use of such vaccines and make them unavailable in many areas in the world. In fact, liquid formulations of Al-based vaccines against diphtheria, pertussis, tetanus, hepatitis B and influenza (type B) should not be frozen (Kartoglu et al., "Validation of the shake test for detecting freeze damage to adsorbed vaccines", *Bull World Health Organ.*, 88:624-631 (2010)). Unfortunately, practices that expose a wide variety of vaccines to sub-zero temperatures are widespread, in both developed and developing countries, across all levels of the respective health systems (Matthias et al., "Freezing temperatures in the vaccine cold chain: a systematic literature review", *Vaccine*, 25:691-697 (2007)).

When a vaccine is damaged by freezing, the potency lost can never be restored, resulting in permanent damage to the underlying composition itself. As a result, freeze-damaged vaccines have lower immunogenicity and are more likely to cause local reactions, such as sterile abscesses (Dimayuga et al., "Effects of freezing on DTP and DTP-IPV vaccines, adsorbed", *Can. Commun. Dis. Rep.*, 21:101-103 (1995); Mansoor et al., "Vaccine adverse events reported in New Zealand", *NZ Med. J.*, 110:270-272 (1997)). Accordingly, much has been devoted to overcoming the inherent problems within the cold chain relative to vaccine compositions.

The cold-chain, a supply chain for pharmaceutical drugs based on temperature control, is a laborious process that attempts to keep vaccines at the suggested 2-8° C. range, and thus costs companies and organizations (ie. UNICEF) millions of dollars every year. Freeze-sensitive vaccines represent over 30% of the $439 million UNICEF spent on all vaccines in 2005 and the $757 million spent in 2010. Carrying-containers using ice (prominent in developing countries), defective refrigerators, and extreme cold climates can impel these vaccines to freeze and render them ineffective. Rate of exposure to freezing temperatures in developed and developing countries is 13.5% and 21.9%, respectively—making this a global concern. Freezing is a risk at any level of the cold chain, and serves as a major problem for many salient vaccines.

In the face of the above mentioned limitations with respect to aluminum-based adjuvants in vaccine compositions, it has been shown that liposomes may be a viable alternative as an adjuvant providing similar immunogenicity, without the problems associated with freeze sensitivity and lyophilization. Furthermore, these freeze sensitive adjuvants found in the prior art have also failed to elicit adequate immune responses in many cases and, often times, do not bind effectively to all protein antigens. This has spurred interest in other forms of adjuvants which may be more versatile and without the encumbrances identified in Al-based adjuvants.

In the approximately 1,400 publications about liposomal vaccines since 1974, over 25% have been published in the past three years, propelling the creation of multiple vaccines using liposomal adjuvants against influenza (Inflexal®V) and hepatitis (Epaxal®). Both of these vaccines must be stored at 2-8° C. and should not be frozen. Other liposomal vaccines that are currently moving toward regulatory approval are based on synthetic, cationic lipids which are insufficiently immunogenic, and are thus often combined with immunostimulators such as lipid A. Similar studies have also proven an effective composition in other alternative, bioactive lipid based vaccine compositions using Lipid A (Coler et al., "Development and Characterization of Synthetic Glucopyranosyl Lipid Adjuvant System as a Vaccine Adjuvant", *PLoS One*, 6:e16333 (2011)).

Liposomes are lipid-bilayer, vesicular structures within which a variety of substances may be entrapped and delivered in vivo in a safe and effective manner. Liposomes are composed largely of natural or synthetic phospholipids which, over the last several decades, have been utilized for effective delivery of therapeutic agents ranging from enzyme replacement therapy (Jain et al., "Muco-adhesive multivesicular liposomes as an effective carrier for transmucosal insulin delivery", *J. Drug Target*, 15:417-427 (2007)), to intracellular delivery of chelating agents in cases of heavy metal poisoning (Rahman et al., "Preparation and prolonged tissue retention of liposome-encapsulated chelating agents", *J. Lab. Clin. Med.*, 83:640-647 (1974)), to even possible treatments for certain cancers (Gregoriadis et al., "Drug-carrier potential of liposomes in cancer chemotherapy", *Lancet*, 1:1313-1316 (1974)).

More recently, liposomes have been found to be suitable vaccine adjuvants in having the ability to prevent antigen degradation while enhancing its uptake by APCs (Gregoriadis et al., "The immunological adjuvant and vaccine carrier properties of liposomes", *J. Drug Target*, 2:351-356 (1994); Brunel et al., "Cationic lipid DC-Chol induces an improved and balanced immunity able to overcome the unresponsiveness to the hepatitis B vaccine", *Vaccine*, 17:2192-2203 (1999)).

Liposomes have been considered as useful vehicles for the containment of particular antigens, though the choice of lipid used in the synthesis of liposomes greatly impacts their physico-chemical and immunogenic properties. Much research has been devoted to the use of many diverse lipids with the aim of refining the adjuvanting effect of liposome-delivered vaccines (Gluck, R., "Liposomal presentation of antigens for human vaccines", *Vaccine Design: The Subunit and Adjuvant Approach.*, 347-361 (1995)). Phospholipid molecules, in particular, have been examined for their distinctive regions of non-polar (comprised of one of more fatty acid chains or cholesterol) and polar (consisting of a phosphate group linked to tertiary or quarternary ammonium salts). The polar region can have a net negative (anionic), neutral or positive (cationic) surface charge, which directly impacts the specific behavior and function of the specific liposome (Milicic et al., "Small cationic DDA:TDB liposomes as protein vaccine adjuvants obviate the need for TLR agonists in inducing cellular and humoral responses", *PLoS ONE*, 7(3):1-10 (2012)).

While the potential of antigens entrapped in liposomes for use as potential vaccines have shown promising results, there are a great many alternatives to preferred liposomal compositions, particularly with respect to entrapment of the antigens. For instance, antigens to be delivered may either be entrapped within the aqueous compartment of the liposomes, incorporated into the lipid bilayer membrane (hydrophobic antigens) or adsorbed into the liposomal surface through covalent or charge-dependent, electrostatic interaction (Taneichi et al., "Induction of differential T-cell epitope by plain- and liposome-coupled antigen", *Bioconjug. Chem.*, 17:899-904 (2006)). More recently, strong evidence has indicated great potential for enhancing immunogenicity of cationic liposomes through addition of toll-like receptor (TLR) agonists (Bal et al., "Co-encapsulation of antigen and toll-like receipt ligand in cationic liposomes affects the quality of the immune response in mice after intradermal vaccination", *Vaccine*, 29:1045-1052 (2011)). Similarly, liposomal encapsulation of CpG oligonucleotides has been shown to enhance and prolong innate system stimulation and advanced the CpG-induced immune protection against *Listeria* (Gursel et al., "Sterically stabilized cationic liposomes improve the uptake and immunostimulatory activity of CpG oligonucleotides", *J. Immunol.*, 167:3324-3328 (2001)).

Methods of manufacturing the antigen loaded liposomes of the prior art consist primarily of embodiments described in the literature involving reverse phase evaporation and related techniques (Sazoka et al., "Rapid separation of low molecular weight solute from liposomes without dilution", *Proc. Natl. Acad. Sci.*, 75:4194 (1978)). With respect to liposomal compositions consisting of glucopyranosyl lipid adjuvant (GLA), the methods used to develop such adjuvants are formulated as aqueous suspensions and have been used in the past to characterize the usefulness of synthetic TLR4 agonists (Anderson et al., "Physicochemical characterization and biological activity of synthetic TLR4 agonist formulations", *Colloids Surf. B. Biointerfaces*, 75:123-132 (2010)). However, many of the known methods of making liposomal vaccines in the prior art have encountered several difficulties, ranging from error in antigen binding to non-specific effects relating to the aqueous suspension. Most importantly, such vaccine formulations still suffer from the general defect found in the Al-based vaccines relating to freeze sensitivity. Thus, there remains a great need in the art to solve the problem of generating a vaccine composition capable of eliciting a consistent immunogenic response, with a high degree of selectivity and efficacy, with such activity not being diminished in the presence of sub-zero temperatures.

SUMMARY OF THE INVENTION

The present invention provides methods and compositions comprising injectable, liposomal vaccines further comprised of members selected from the group consisting of natural lipids, dipalmitoyl phosphatidylcholine (DPPC), dioleoyl phosphatidylcholine (DOPC) and cholesterol with either a negatively charged lipid comprising dipalmitoyl phosphatidylglycerol (DPPG) or a positively charged lipid comprising stearylamine (SA).

In one aspect, the present invention provides for a composition comprising at least one of DPPC, DOPC, cholesterol and a charged lipid with an entrapped or adsorbed protein antigen capable of inducing an antibody response against an antigen in a subject. An alternative embodiment provides for a cationic liposomal vaccine composition comprising DPPC:DOPC:cholesterol:SA in a molar ratio of approximately 40:20-30:20:10-20 and wherein the cationic liposomal vaccine is formulated as a lyophilized composition. Preferably, the molar ratio of DPPC:DOPC:cholesterol:SA is 40:25:20:15. Optionally, the cationic liposomal vaccine is formulated as an aqueous solution.

Another alternative embodiment in the compositions of the present invention provides for an anionic liposomal vaccine composition comprising DPPC:DOPC:cholesterol:DPPG in a molar ratio of approximately 40:20-30:20:10-20 and wherein the anionic liposomal vaccine is formulated as a lyophilized composition. Preferably, the molar ratio of DPPC:DOPC:cholesterol:DPPG is 40:25:20:15. Optionally, the anionic liposomal vaccine is formulated as an aqueous solution.

In another aspect, the positively charged lipid is at least one selected from the group consisting of stearylamine (SA), dioleoyl trimethylammoniumpropane (DOTAP), dimethyldioctadecylammonium (DDAB), ethylphosphocholine (Ethyl PC), dipalmitoyl trimethylammoniumpropane (DPTAP) and dipalmitoyl trimethylammonium (DPTMA), as well as variants thereof. In another aspect, the negatively charged lipid is at least one selected from the group consisting of dipalmitoyl phosphate (DPPA), dipalmitoyl phosphatidylglycerol (DPPG), dihexadecanoyl phosphoserine (DPPS), and ditetradecyl phosphoglycerol (Diether PG), as well as variants thereof.

In yet another aspect, the present invention provides for methods of manufacturing a liposomal vaccine composition comprising: (a) providing a lipid blend, further comprising at least a pair of natural lipids consisting of at least one saturated natural lipid and at least one unsaturated natural lipid, and cholesterol; (h) combining the lipid blend together with the cholesterol; (c) dissolving (b) in a cosolvent; (d) drying (c) in a water bath under nitrogen gas at a temperature above the gel to liquid crystalline temperature of the lipids (about 50° C.) to form a homogenous lipid-blend film (e) placing (d) under vacuum to remove the residual solvent; (f) hydrating (e) with an effective amount of at least one antigen solution; and (g) agitating (f) to form multi lamellar vesicles (MLVs) with entrapped or adsorbed antigen, wherein the liposomal vaccine composition is freeze stable.

Implementations of the above aspects can include one or more of the following: Liposomes consisting of a vaccine composition comprising of DPPC, DOPC, cholesterol and a charged lipid, with an entrapped or adsorbed protein antigen capable of inducing an antibody response against the antigen in a subject. Preferably, liposomes can be used as an adjuvant. Additionally, the liposomes can be used as a means for entrapment of an antigen in a vaccine composition. Liposomes of the present invention do not lose their immunogenicity after being exposed to freezing temperatures during multiple freeze-thaws. Preferably, the adjuvants of the present invention are freeze-stable adjuvants.

In another aspect, the composition of the present invention is preferably in a molar ratio of 40:25:20 of DPPC:DOPC:cholesterol and 15 for a negatively charged lipid. Preferably, the negatively charged lipid is DPPG. The composition is preferably in a molar ratio of 40:25:20 of DPPC:DOPC:cholesterol and 15 for a positively charged lipid. Preferably, the positively charged lipid is SA. Preferably, the composition is capable of being stable in freezing temperatures and retaining immunogenic activity after more than one freeze-thaw cycles, further wherein the composition is finally freeze-dried at a temperature of about −45° C.

The mean hydrodynamic particle diameter of the liposomes of the present invention is in the size range of 300-1000 nm. Preferably, the composition comprising the liposomes maintains immunogenicity after lyophilization at a freezing temperature range between about −30° C. to about −50° C. in the presence of a lyoprotectant (e.g. sucrose or trehalose). The adjuvant liposomes of the present invention can be used as an alternative to freeze-sensitive aluminum salt adjuvants in all vaccine formulations containing these adjuvants.

In another aspect, the protein antigen can be selected from or derived from the group consisting of rotavirus, foot and mouth disease virus, influenza A virus, influenza B virus, influenza C virus, H1N1, H2N2, H3N2, H5N1, H7N7, H1N2, H9N2, H7N2, H7N3, H10N7, human parainfluenza type 2, herpes simplex virus, Epstein-Barr virus, varicella virus, porcine herpesvirus 1, cytomegalovirus, lyssavirus, *Bacillus anthracis*, anthrax PA and derivatives, poliovirus, hepatitis A, hepatitis B, hepatitis C, hepatitis E, distemper virus, Venezuelan equine encephalomyelitis, feline leukemia virus, reovirus, respiratory syncytial virus, Lassa fever virus, polyoma tumor virus, canine parvovirus, papilloma virus, tick borne encephalitis virus, rinderpest virus, human rhinovirus species, Enterovirus species, Mengovirus, paramyxovirus, avian infectious bronchitis virus, human T-cell leukemia-lymphoma virus 1, human immunodeficiency virus-1, human immunodeficiency virus-2, lymphocytic choriomeningitis virus, parvovirus B19, adenovirus, rubella virus, yellow fever virus, dengue virus, bovine respiratory syncitial virus, corona virus, *Bordetella pertussis, Bordetella bronchiseptica, Bordetella parapertussis, Brucella abortis, Brucella melitensis, Brucella suis, Brucella ovis, Brucella* species, *Escherichia coli, Salmonella* species, *Salmonella typhi, Streptococci, Vibrio cholera, Vibrio parahaemolyticus, Shigella, Pseudomonas, tuberculosis, avium, Bacille Calmette Guerin, Mycobacterium leprae, Pneumococci, Staphylococci, Enterobacter* species, *Rochalimaia henselae, Pasteurella haemolytica, Pasteurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia rickettsii, Rickettsia typhi, Rickettsia prowsaekii, Ehrlichia chaffeensis, Anaplasma phagocytophilum, Plasmodium falciparum, Plasmodium vivax, Plasmodium malariae, Schistosomes, trypanosomes, Leishmania* species, *Filarial nematodes, trichomoniasis, sarcosporidiasis, Taenia saginata, Taenia solium, Leishmania, Toxoplasma gondii, Trichinella spiralis, coccidiosis, Eimeria tenella, Cryptococcus neoformans, Candida albican, Apergillus fumigatus, coccidioidomycosis, Neisseria gonorrhoeae*, malaria circumsporozoite protein, malaria merozoite protein, trypanosome surface antigen protein, pertussis, alphaviruses, adenovirus, diphtheria toxoid, tetanus toxoid, meningococcal outer membrane protein, streptococcal M protein, Influenza hemagglutinin, cancer antigen, tumor antigens, toxins, *Clostridium perfringens* epsilon toxin, ricin toxin, pseudomonas exotoxin, exotoxins, neurotoxins, cytokines, cytokine receptors, monokines, monokine receptors, plant pollens, animal dander, and dust mites. The particles can be used in formulation of vaccines against diphtheria, tetanus, pertussis (whooping cough), influenza, hepatitis B, botulinium toxin, anthrax, or combination vaccines such as, PedvaxHIB (Haemophilus b Conjugate and Meninococcal Protein Conjugate), Comvax® (Meningococcal Protein Conjugate and Hepatitis B, recombinant antigens), Tripedia® (Diphtheria and Tetanus Toxoids and Acellular Pertussis antigens). Infaniix® (Diphtheria and Tetanus Toxoids and Acellular Pertussis antigens), or any other vaccines that loses its potency upon freezing.

In yet another aspect, the present invention provides for using a novel lipid composition as an adjuvant, wherein the liposomal vaccine is prepared with at least one entrapped antigen having an immunogenic response in a subject. In a preferred embodiment, the lipid composition maintains its immunogenic activity after freezing and lyophilization. Optionally, the at least one entrapped antigen may be selected from the group consisting of polynucleotides, polypeptides, recombinant proteins, synthetic peptides, protein extract, cells (including tumor cells), tissues, polysaccharides and lipids, including fragments thereof.

In another preferred aspect, the liposomal compositions of the present invention do not require the presence of a co-adjuvant such that the methods and compositions of the present invention do not include the following: Lipid A, Lipid A derivatives, monophosphoryl lipid A, monophosphoryl lipid A derivatives, lipopolysaccharide, muramyl dipeptide, CpG containing oligonucleotides, TLR-4 agonists, flagellin, flagellins derived from gram negative bacteria, TLR-5 agonists, fragments of flagellins capable of binding to TLR-5 receptors, saponins, analogues of saponins, QS-21, purified saponin fractions, immune stimulating complexes (ISCOMS) and saponin combinations with sterols. In a preferred embodiment, the methods and compositions of the present invention provide compositions having at least one antigen and lacking a co-adjuvant, wherein the compositions retain their immunogenicity after exposure to freezing temperatures, after multiple freeze-thaws, and after being freeze-dried or lyophilized.

Such liposomal vaccine products offer numerous advantages over Al-based vaccines in regards to safety, freeze-stability, tolerability, biodegradability, and versatility. Hence, this unique liposomal based adjuvant can be employed instead of Al adjuvants in current freeze sensitive vaccines against for example diphtheria, tetanus, pertussis (whooping cough), influenza and anthrax. The novel vaccine adjuvant designed thus provides a technological platform for development of immunogenic, freeze-stable vaccines, preventing product damage during accidental freezing in the cold chain.

Although liposomes have been used before as vaccines (Powell et al., *Vaccine Design, The subunit and Adjuvant Approach, Pharm. Biotech,* 6:159 (1995), the liposomal vaccine described herein as a preferred embodiment of the present invention is composed of natural or synthetic lipids and does not require the addition of immune adjuvants such as Lipid A derivatives. Hence, the rigid liposomal vaccine described in the present invention is of a novel composition of a specific size range that can act as a replacement for Al-based vaccines. These liposomes, because of their lipid composition and size, may also have targeting properties to specific antigen presenting cells or other immunomodulatory cell types and may induce both humoral and cell mediated immune response.

BRIEF DESCRIPTION OF THE DRAWINGS

FIG. 3 shows an exemplary average amount of mouse anti-lysozyme antibody for different formulations (mg/ml).

Figure 6:
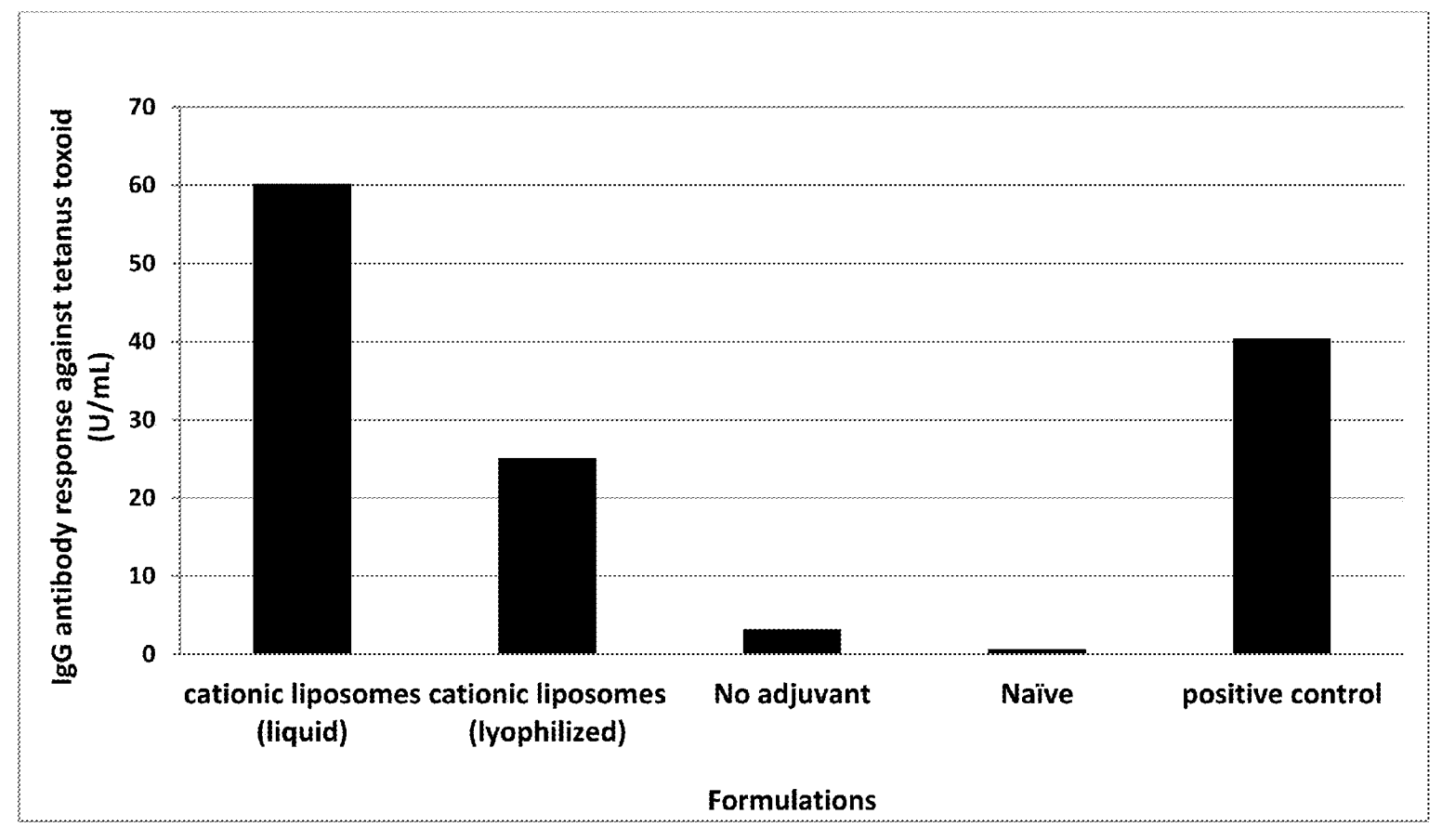

FIG. 6 shows results from a mouse immunogenicity study, wherein the average titers of mouse anti-tetanus toxoid IgG from 5 mice are compared against each formulation. These are the same data from FIG. 8, but without correcting for 100× dilution factors and background (naïve mouse).

FIG. 12 shows the average amount of mouse anti-tetanus antibody for anionic liposome with TLC at 0.4 µg/ml as compared to TLC without adjuvant (Study 2). The bars show the standard deviations.

DETAILED DESCRIPTION OF THE INVENTION

Definitions

Figure 1:
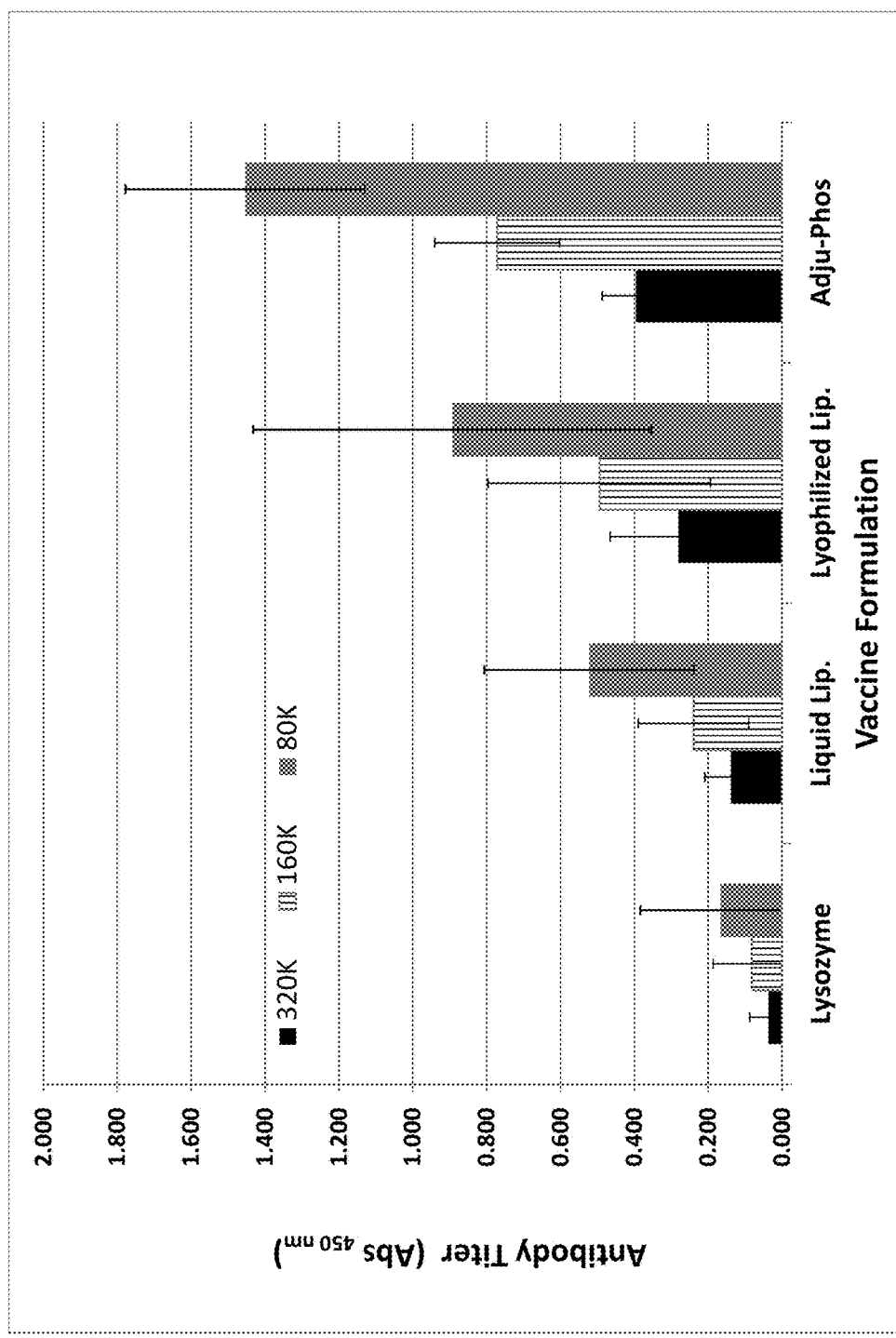
FIG. 1 shows an exemplary immune response (450 nm absorbance) of the various formulations at different dilutions of the sera—80,000, 160,000, and 320,000-fold. The amount of absorbance at 450 nm reflects the amount of antibody present in the sera.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

As used herein, the term "adjuvant" refers to a pharmacological or immunological agent that, when added to vaccines, have the ability to stimulate a subject's immune system's response to a target antigen, but do not, individually, confer immunity. Adjuvants may act in a variety of ways in their presentation of an antigen to the immune system, including but not limited to, acting as a depot or a housing for the antigen (such as liposomes), wherein the antigen is presented over an extended period of time, therefore maximizing the immune response prior to the body's clearance of such antigen.

As used herein, the term "antigen" refers to any substance which provokes an adaptive immune response including, but not limited to, killed, inactivated, attenuated, or modified live bacteria, viruses, or parasites. The term may also include polynucleotides, polypeptides, recombinant proteins, synthetic peptides, protein extract, cells (including tumor cells), tissues, polysaccharides, or lipids, or fragments thereof, individually or in any combination thereof. The term may also include antibodies, such as anti-idiotype antibodies or fragments thereof, and to synthetic peptide mimotopes that can mimic an antigen or antigenic determinant.

As used herein, the term "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

As used herein, the term "cholesterol" refers to a white crystalline substance with a chemical formula of $C_{27}H_{45}OH$. It is a cyclic hydrocarbon alcohol, which is classified as a lipid. It is insoluble in water but soluble in a number of organic solvents.

As used herein, the term "immune response" of a subject shall mean the development of a humoral immune response, a cellular immune response, or a humoral and a cellular immune response to an antigen.

As used herein, the term "immunogenic" shall mean capable of evoking an immune or antigenic response in a subject.

As used herein, the term "immunologically protective amount" or "immunologically effective amount" refers to the quantity or amount sufficient to induce an immunogenic response in a subject. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

As used herein, the term "lipids" refers to any of a group of organic compounds, including the fats, oils, waxes, sterols, and triglycerides, that are insoluble in water but soluble in nonpolar organic solvents, are oily to the touch, and together with carbohydrates and proteins constitute the principal structural material of living cells.

As used herein, the term "liposome" shall mean a microscopic spherical particle formed by a lipid bilayer enclosing an aqueous compartment and capable of entrapping or housing a drug, antigen, vaccine, enzyme or another substance capable of being targeted to cells in the body.

As used herein, the term "lyoprotectant" refers to stabilizers used to prevent denaturation of proteins during freeze-drying and subsequent storage. In order to be effective, lyoprotectants must be retained amorphous. Lyoprotectants of the present invention include, but are not limited to, trehalose, sucrose and mannitol.

As used herein, the term "subject" refers to any animal, including humans, for which the administration of an adjuvant composition is desired. It includes mammals and non-mammals, including primates, livestock, companion animals, laboratory test animals, captive wild animals, ayes (including in ova), reptiles, and fish.

As used herein, the term "vaccine" shall mean any composition that includes an antigen, the administration of which resulting in an immune response in a subject having received such administration.

The present invention describes methods and compositions related to freeze stable vaccines in order to overcome the inherent problems identified in the vaccines of the state of the art. Presently, for instance, there are numerous vaccines on the market against tetanus toxoid, a sampling of which is noted at Table 1.

TABLE 1

List of Tetanus vaccines currently in the market

| Vaccine | Description | Manufacturer | Storage Condition |
| --- | --- | --- | --- |
| PEDIAEIX (Diphtheria and Tetanus Toxoids and Acellular Pertussis Adsorbed, Hepatitis B (Recombinant) and Inactivated Poliovirus Vaccine) | Suspension for Intramuscular Injection | GSK | 2-8° C., Do NOT FREEZE, discard if frozen |
| Adacel (Tetanus Toxoid, Reduced Diphtheria Toxoid and Acellular Pertussis Vaccine Adsorbed) | Single-dose vials and prefilled syringes containing a 0.5-mL suspension for im injection. | Sanofi | Store between 2°-8° C. (35°-46° F.). DO NOT FREEZE. Discard product if exposed to freezing. |
| BOOSTRIX (Tetanus Toxoid, Reduced Diphtheria Toxoid and Acellular Pertussis Vaccine, Adsorbed) | Single-dose vials and prefilled syringes containing a 0.5-mL suspension for im injection | GSK | 2-8° C., Do NOT FREEZE, discard if frozen |
| DAPTACEL (Diphtheria and Tetanus Toxoids and Acellular Pertussis Vaccine Adsorbed) | Suspension for im injection, supplied in single dose (0.5 mL) vials | Sanofi | 2-8° C., Do NOT FREEZE, discard if frozen |
| Pentacel (Diphtheria and Tetanus Toxoids and Acellular Pertussis Adsorbed, Inactivated Poliovirus and *Haemophilus* b Conjugate (Tetanus Toxoid Conjugate) Vaccine Suspension for Intramuscular Injection | Pentacel consists of a liquid vaccine component (DTaP-IPV component) and a lyophilized vaccine component (ActHIB vaccine). Reconstitute the ActHIB vaccine component with the DTaP-IPV component immediately before administration. | Sanofi | Store the DTaP-IPV vial and the Hib vial in the original box in the refrigerator at 35°-46° F. (2°-8° C.). Protect from light. Do not freeze! |
| INFANRIX (Diphtheria and Tetanus ds and Acellular Pertussis ne Adsorbed) | Single-dose vials and prefilled syringes containing a 0.5-mL suspension for injection. Suspension for Intramuscular Injection | GSK | Store refrigerated between 2° and 8° C. (36° and 46° F.). Do not freeze. Discard if the vaccine has been frozen. |
| KINRIX (Diphtheria and Tetanus Toxoids and Acellular Pertussis Adsorbed and Inactivated Poliovirus Vaccine) Suspension for Intramuscular Injection | A single intramuscular injection (0.5 mL). Single-dose vials and prefilled syringes containing a 0.5-mL suspension for injection. | GSK | Store refrigerated between 2° and 8° C. (36° and 46° F.). Do not freeze. Discard if the vaccine has been frozen. |
| ActHIB ®, *Haemophilus* b Conjugate Vaccine (Tetanus Toxoid Conjugate), produced by Sanofi Pasteur SA, is a sterile, lyophilized powder which is reconstituted at the time of use with either saline diluent (0.4% Sodium Chloride) | ActHIB VACCINE RECONSTITUTED WITH 0.4% SODIUM CHLORIDE DILUENT Vial, 1 Dose, lyophilized vaccine (5 × 1 Dose vials per package), packaged with 0.6 mL vial containing diluent (5 × 0.6 mL vials per package) (contains NO preservative). | Sanofi | Store lyophilized vaccine packaged with saline diluent, Diphtheria and Tetanus Toxoids and Pertussis or Tripedia vaccine at 2° to 8° C. (35° to 46° F.). DO NOT FREEZE. |
| TENIVAC (Tetanus and Diphtheria Toxoids Adsorbed) Suspension for Intramuscular Injection | Suspension for injection supplied in 0.5 mL single-dose vials or syringes | Sanofi | Should be stored at 2° to 8° C. (35° to 46° F.). DO NOT FREEZE. |
| Td (generic) Tetanus and Diphtheria Toxoids Adsorbed (Td) | Asterile vaccine for intramuscular injection. Includes a traceamount of thimerosal [mercury derivative, (≤0.3 mcg mercury/dose)] (not as a preservative) from the manufacturing process. The tetanus and diphtheria toxoids induce at least 2 units and 1 unit of antitoxin per ml of serum, respectively, in the guinea pig potency test. | MassBiologics | Store at 2° C.-8° C. (36° F.-46° F.). DO NOT FREEZE. Discard product if exposed to freezing |

As evidenced by Table 1, all of the tetanus vaccines currently out in the market employ an adjuvant system that requires a storage environment at some temperature range above zero (ie. 2° C.-8° C.) but no more than 10° C. for any period of time. More importantly, for the vast majority of these vaccines, instruction is provided that, should the vaccines be exposed to freezing (ie. sub-zero) temperatures, the product should be discarded.

The immunogenicity of a new liposomal adjuvant consisting of a lipid blend composition comprising the following lipids: Dipalmitoyl phosphatidylcholine (DPPC), Dioleoyl phosphatidylcholine (DOPC), Cholesterol was tested with either a negative charge lipid: Dipalmitoyl phosphatidylglycerol (DPPG) in Example 1 or with a positively charged lipid: Octadecylamine (Stearylamine, SA) in Example 2. In these embodiments the molar ratio of DPPC:DOPC:cholesterol was 40:25:20 and that of the charged lipid was 15. Chicken egg lysozyme and tetanus light chain (TLC) were used as model protein antigens, respectively. The charged liposomal adjuvants with the associated protein antigen were immunogenic and did not lose their immunogenic activity after multiple freeze-thaw cycles and also additional freezing to −40° C. during lyophilization. Thus, they can be used in vaccine formulations as an alternative to Aluminum salt adjuvants.

The vaccine adjuvant designed provides a technological platform for development of immunogenic, freeze-stable vaccines, preventing product damage during accidental freezing in the cold chain. The liposomal vaccine adjuvant can be used to develop vaccines that are stable against freezing. The novel freeze-dried liposomal vaccine demonstrated efficacy similar to that of a liquid aluminum-phosphate based vaccine as measured by the antibody response to an antigen, preferably lysozyme, in mice. The results showed that the liposomal vaccine was freeze-stable and did not lose its immunogenic activity upon freezing/freeze-drying.

Such a liposomal vaccine product offers numerous advantages over aluminum-based vaccines in regards to safety, freeze-stability, tolerability, biodegradability, and versatility. It is recommended to use this adjuvant instead of aluminum-based adjuvants in current freeze sensitive vaccines against for example diphtheria, tetanus, pertussis (whooping cough), influenza and anthrax. The novel vaccine adjuvant designed thus provides a technological platform for development of immunogenic, freeze-stable vaccines, preventing product damage during accidental freezing in the cold chain.

EXAMPLES

I. Vaccine Preparation Using Lysozyme as the Antigen

Vaccine Preparation

The immunogenicity of a lysozyme-liposomal vaccine (Lipo-Lyz) was investigated before and after freeze-drying (Formulations 1 and 2, respectively). Lysozyme adsorbed to Adju-Phos® (Adju-Lyz) was used as an aluminum salt based vaccine reference. Also a solution of lysozyme without adjuvant was used as a reference. The four different formulations are summarized in Table 2. All formulations were prepared in a laminar flow hood using depyrogenated vials and utensils, as it is described below.

TABLE 2

Formulation descriptions

| Formulation | Adjuvant | Antigen | Lyoprotectant | Dosage form |
|---|---|---|---|---|
| 1 | DPPC/DPPG/ DOPC/Cholesterol (Lipo-Lyz (Aq)) | Chicken Egg Lysozyme | Sucrose | Liquid |
| 2 | DPPC/DPPG/ DOPC/Cholesterol (Lipo-Lyz (FD)) | Chicken Egg Lysozyme | Sucrose | Lyophilized |
| 3 | Aluminum phosphate (Adju-Phos ®) (Adju-Lyz (Aq)) | Chicken Egg Lysozyme | Sucrose | Liquid |
| 4 | None (Lyz) | Chicken Egg Lysozyme | Sucrose | Liquid |

Preparation of a 9 Mg/ml Stock Lysozyme Solution in PBS

In order to prepare 1 L phosphate buffer saline (PBS), 1 pouch PBS powder was dissolved in 1 L water for injection (WFI). The mixture was then stirred on a magnetic stirrer for 5 minutes. The solution was then filtered through a 0.22 um Polyvinylidene Difluoride (PVDF) filter, using a Corning 1 L Filter System and a vacuum pump.

50.1 mg lysozyme was weighed using an analytical balance. 5 ml of PBS was measured using a sterile, 5 ml pipette and added to the lysozyme powder. The solution was stirred on a magnetic stirrer for 3 minutes until the solution was dissolved. The solution was then filtered through a 0.22 μm sterile filter. The actual concentration of lysozyme in the filtered solution was determined by UV Spectrophotometry. This stock solution was used in preparation of different vaccine formulations.

Preparation of Liquid and Lyophilized Liposomal Vaccines (Formulations 1 & 2)

Specific amounts of DPPC, DOPC, cholesterol and DPPG in a molar ratio of 40:25:20:15 were dissolved in a co-solvent containing chloroform, methanol, and water. The lipid blend was dried in a 45° C. water bath under a stream of nitrogen gas, and any remaining residual solvent was removed under vacuum overnight to ensure complete desiccation.

The dried lipid-blend (50 mg) was hydrated in 1 ml of an 8.9 mg/ml lysozyme stock solution and vortexed to form MLVs. In order to improve the entrapping efficacy, the liposome solution was freeze-thawed five times using an acetone-ice bath and a warm-water bath. The liposome mixture was centrifuged at 14,000 rpm for 20 min to separate the liposomes from the unbound lysozyme solution. The unbound lysozyme in supernatant was removed and the amount of unbound lysozyme in the supernatant was determined by UV spectroscopy (n=3). The average unbound concentration was subtracted from the initial lysozyme concentration to acquire the concentration of bound/entrapped lysozyme.

The liposome pellet containing entrapped lysozyme was resuspended in 1 ml of a sterile filtered 10% w/w sucrose solution and vortexed. To reduce the size of liposomes and to obtain a more homogenous particle distribution, the liposome solution was extruded five times through two 800 nm polycarbonate filters in a 10 ml extruder using nitrogen gas at pressures around 50-100 psi. Lysozyme concentration in the concentrated liposome solution was determined and adjusted to 200 μg/ml by diluting the solution in 10% sucrose. The lysozyme concentration in the final solution was determined by UV spectroscopy.

Eight vials were filled with 1 ml of liposome solution each. Four of the vials were freeze-dried in a lyophilizer by first freezing the solution at −45° C. at 1° C./min and holding it at this temperature for 2 hours. Primary drying was performed at −20° C. shelf temperature for 20 hours at a chamber pressure of 150 mTorr. After primary drying, the shelf temperature was increased to 25° C. at a rate of 0.2° C./min. Secondary drying was performed at 25° C. shelf temperature for 10 hours at a chamber pressure of 100 mTorr.

Preparation of 200 μg/ml Lysozyme/Adju-Phos® Vaccines (Formulation 3)

In order to prepare an aluminum salt based vaccine, 0.5 ml of 8.9 mg/ml lysozyme stock solution and 1 ml 2% (20 mg/ml) Adju-Phos® suspension were mixed in a 1.5 ml centrifuge tube and stored for 42 minutes at room temperature to allow for lysozyme to be adsorbed to Adju-Phos. The mixture was then centrifuged for 5 min at 5,000 rpm to pellet the adsorbed lysozyme-Adju-Phos® complex. The supernatant was removed and measured by UV spectroscopy to determine the amount of unbound lysozyme. The concentration of bound lysozyme was determined by subtracting this value from the initial added amount. Based on the amount of bound lysozyme, 10% sucrose solution was added to the Adju-Phos®/lysozyme pellet to acquire a total weight of 28 g. This would give an adjuvant:antigen ratio of 24 w/w, i.e. similar to that used in Lipo-formulations (Formulations 1 and 2), further described in Table 3.

TABLE 3

Final Formulation Target Concentration (mg/ml) and Ratios

| Formulation | Name | Target Adjuvant Concentration (mg/mL) | Target Lyzosyme Concentration (mg/mL) | Target ratio (Adjuvant/Lyz) |
|---|---|---|---|---|
| 1 | Lipo-Lyz (Aq) | 5 | 0.20 | 25 |
| 2 | Lipo-Lyz(Lyo) | 5 | 0.20 | 25 |
| 3 | Adju-Lyz (Aq) | 0.71 | 0.03 | 24 |
| 4 | Lyz | 0 | 0.20 | 0 |

Preparation of Lysozyme with No Adjuvant in 10% Sucrose (Formulation 4)

In order to prepare a lysozyme solution with no adjuvant, 10 ml of 200 μg/ml lysozyme solution was prepared by diluting 226 μl lysozyme stock solution (8.9 mg/ml) with 10% sucrose until a total weight of 10 g was obtained. Concentration of lysozyme in the final formulation was determined by UV spectroscopy.

UV Spectroscopy

50 μl of each sample was diluted in PBS as needed and analyzed in an Agilent 8453 UV spectrophotometer (Agilent Technologies, USA) equipped with a Peltier cell holder at 20° C. and a 1 cm path length quartz cell was used. Data was collected in a wavelength range of 200-500 nm, with an integration time of 10 seconds at 1 nm intervals. The concentration of lysozyme was determined by Eqn. 1.

$$C=(A_{280}-Abs_{LS280})/\epsilon. \qquad \text{(Eqn. 1)}$$

Where $Abs_{LS280}$ is the light scattering interference at 280 nm determined by logarithmic regression extrapolation through absorbencies at 320 and 350 nm, and $A_{280}$ is the absorbance at 280 nm. An extinction coefficient ($\epsilon$) of 2.63 ml/(mg×cm) was used to calculate the lysozyme concentration (C) in mg/ml according to Eqn 1. The average concentration of lysozyme was calculated based on three readings.

Particle Size Characterization Using Dynamic Light Scattering (DLS)

All samples were analyzed on a Precision Detector DLS instrument PD2000DLSP$^{plus}$ and PDDLS/CoolBatch 90T using quartz cuvettes (Precision Detectors). Measurements were done at 20° C. using a refractive index of 1.3330 and a viscosity of 0.01002 Poise. Sample time was 15 μsec and 3 sec run duration with a total of 60 accumulations per measurement. Data was analyzed using Precision Deconvolve software. Each sample was analyzed in triplicate. The mean hydrodynamic diameter by intensity and standard deviation (SD) were calculated (n=3).

For the liposomal formulations, the mean particle diameter was also determined after one year storage of the samples at 2-8° C. The lyophilized liposome sample was also stored at room temperature more than two years. This sample was reconstituted and analyzed by DLS (Table 6b).

Mice Immunization

100 μl (2×50 μl) of each formulation was injected intramuscularly (IM) in the shoulder of four female CD-1 mice (Charles River, Hollister Calif.). A booster shot was administered on day 14. Twenty mice were tested in groups of four. 16 were used for vaccine testing and 4 were naïve mice as negative control. All of the animals were observed immediately after dosing and daily thereafter. On Day 28, serum was collected from the immunized mice as well as the control group and the antibody response to each vaccine was determined by Indirect Enzyme-Linked Immunosorbent Assay (Indirect ELISA) to chicken egg lysozyme.

Statistical analysis of the induced immune responses was performed, including a two-tail t-test. Differences were considered significant if p<0.05.

The study design and group designation are summarized in Table 4.

TABLE 4

Study Group Designations

| Group/ Test Article # | No. mice/ group | Dose Volume | Sex | Day 0 - Dose | Day 14 - Dose | Day 28 Terminal Bleed |
|---|---|---|---|---|---|---|
| 1 | 4 | 100 μl in two sites | F | Intramuscular | Intramuscular | Cardiac Puncture |
| 2 | 4 | 100 μl in two sites | F | Intramuscular | Intramuscular | Cardiac Puncture |
| 3 | 4 | 100 μl in two sites | F | Intramuscular | Intramuscular | Cardiac Puncture |
| 4 | 4 | 100 μl in two sites | F | Intramuscular | Intramuscular | Cardiac Puncture |
| 5 (naïve animals) | 4 | N/A | F | None - Naïve Animals | | Cardiac Puncture |

Prior to dosing, animals will be arbitrarily assigned to treatment groups. On Day 0, each mouse will be injected IM with 100 μl of test article (50 μl in each shoulder) using an appropriate size syringe and beveled needle (i.e. 1 cc insulin syringe w/26 gauge (or smaller) needle).

Group 1 was dosed with Formulation 1 (Lipo-Lyz (Aq)); Group 2 was dosed with Formulation 2 (Lipo-Lyz (Lyo)); Group 3 was dosed with Formulation 3 (Adju-Lyz (Aq)); Group 4 was dosed with Formulation 4 (Lyz). Group 5 animals were naïve animals and did not receive any test article. On Day 14, each animal received a booster injection of the appropriate test article. On Day 28, animals were exsanguinated via cardiac puncture.

The blood was collected into tubes containing no anticoagulant. The tubes were centrifuged at ~2800 rpm for at least 10 minutes. Sera were placed into appropriately labeled tubes and stored at −16° C. to −22° C. until analysis by ELISA for chicken egg lysozyme IgG antibodies.

Test Article Preparation

Group 1: SP-255a: Formulation 1 (lysozyme+liposomes): One vial was used per scheduled dosing time point for all animals in the dose group. Prior to injection, the vial was gently inverted at least 10 times and then gently swirled to obtain a homogenous mixture.

Group 2: SP-255b: Formulation 2 (lyophilized lysozyme+ liposomes): One lyophilized vial and one diluent vial was used per scheduled dosing time point for all animals in the dose group. Prior to injection, the lyophilized cake was reconstituted with 1 ml of diluent. The reconstituted vial was swirled to obtain a homogenous mixture.

Group 3: SP-256a, Formulation 3 (lysozyme+Adju-Phos): One vial was used per scheduled dosing time point for all animals in the dose group. The vial was vigorously shaken to obtain good homogeneity.

Group 4: SP-256b, Formulation 4 (lysozyme in 10% sucrose): One vial was used per scheduled dosing time point for all animals in the dose group. Prior to injection, the vial was gently inverted at least 10 times and then gently swirled to obtain a homogenous mixture.

Group 5: Naïve animals; no test article was administered.

Dosing Procedure

Four groups of 4 CD-1 female mice were dosed intramuscularly with 100 μl of test article on Day 0 and Day 14. Serum was collected from each animal on Day 28. Additionally, serum was collected from 4 naïve female CD-1 mice on Day 28 as a control group. The serum was frozen and stored at −80° C. until analysis by ELISA for chicken egg lysozyme IgG antibodies.

Determination of Amount Bound and Unbound Lysozyme

The concentration of lysozyme stock solution, unbound and bound lysozyme, was determined by UV spectroscopy. The results are listed in Table 5. According to these results, the concentration of lysozyme stock solution was 8.9 mg/ml (±0.1), the concentration of free lysozyme in the supernatant was determined to be 5.9 mg/ml (±0.0) out of 8.9 in the liposome-lysozyme solution supernatant and 2.2 (+0.0) mg/ml (out of 3.0 mg/ml) in the Adju-Phos®-lysozyme supernatant. The amounts of bound/entrapped lysozyme to Adju-Phos®/liposomes were thus 26% w/w and 34% w/w, respectively. These values are in the expected range.

TABLE 5

Measurements of Bound and Unbound Lysozyme

| No | Name | Adjuvant Concentration (mg/mL) | Lysozyme Concentration (mg/mL) | Initial Adjuvant/Lyz | Unbound/ free (mg/mL) | Bound (mg/mL) | Entrapped (%) |
|---|---|---|---|---|---|---|---|
| 1 | Lipo-Lyz(Aq) | 50 | 8.9 ± 0.1 | 5.6 | 5.9 ± 0.0 | 3.0 ± 0.0 | 34 |
| 2 | Lipo-Lyz (Lyo) | 50 | 8.9 ± 0.1 | 5.6 | 5.9 ± 0.0 | 3.0 ± 0.0 | 34 |
| 3 | Adju-Lyz (Aq) | 20 | 3.0 ± 0.1 | 6.7 | 2.2 ± 0.0 | 0.8 ± 0.0 | 26 |
| 4 | Lyz | 0 | 8.9 ± 0.1 | 0 | — | — | — |

Lysozyme Concentration in Final Vaccine Formulations

As shown in Table 6, the average lysozyme concentrations in liquid and lyophilized liposomal vaccines were 0.26 mg/ml (±0.01 mg/ml) and 0.27 mg/ml (±0.03 mg/ml), respectively.

The concentration of lysozyme in the liquid Adju-Phos® formulation and in the lysozyme solution with no adjuvant were 0.03 (±0.00 mg/ml) and 0.22 mg/ml (±0.00 mg/ml), respectively and as expected.

Particle Size Characterization Using Dynamic Light Scattering (DLS)

The particle size data are shown in Tables 6 and 7. The mean hydrodynamic particle diameters of liposomes from distributions by intensity, before and after lyophilization were 707 nm (±5 nm) and 667 nm (±113 nm), respectively. No significant change in particle diameter was thus observed before and after freeze-drying of liposomes. When these samples were characterized after one year storage at 5° C., the mean particle diameter were relatively unchanged with the corresponding values of 639 nm (±6 nm) and 647 nm (±14 nm) for the liquid and lyophilized liposomes, respectively (Table 7a, b).

The mean particle diameter for the lyophilized liposomal vaccine sample that was stored at room temperature for 28 months (Table 7b) was 691 nm±58 nm. Surprisingly, after 2 years of storage of the lyophilized vaccine at room temperature, the particle size of liposomes is unchanged and no aggregation is observed.

The average particle size in Adju-Lyz formulation was >2000 nm and thus outside the range of the DLS instrument. According to literature, the particle size of Adju-Phos® is in the range of 1-10 μm. The mean hydrodynamic diameter of lysozyme in solution was 8.4±1.4 nm (Table 6).

TABLE 6

Characterization of Final Vaccine Formulations, Mean Particle Diameters and Antibody Titers of the Vaccines

| Vaccine | Measured Lysozyme (mg/ml) Mean (±SD) | Particle diameter (nm) Mean (±SD) | Antibody titer (mg/ml) Mean (±SD) |
|---|---|---|---|
| Lipo-Lyz (Aq) | 0.26 (±0.01) | 707 (±5) | 177 (±68) |
| Lipo-Lyz (Lyo) | 0.27 (±0.03) | 667 (±113) | 306 (±207) |
| Adju-Lyz (Aq) | 0.03 (±0.00) | >2000[a] | 478 (±136) |
| Lyz (Aq) | 0.22 (±0.00) | 8.4 (±1.4) | 50 (±50) |

[a]Particles were outside the upper size limit of the DLS instrument and could not be measured accurately TABLE 7a Stability of Liquid Liposomal Vaccine Formulation of Lysozyme (Lipo-Lyz (Aq))

| Vaccine | Measured Lysozyme (mg/ml) Mean (±SD) | Particle diameter (nm) Mean (±SD) | Antibody titer (mg/ml) Mean (±SD) |
|---|---|---|---|
| t0 | 0.26 (±0.01) | 707 (±5) | 177 (±68) |
| 13 months | ND | 639 (±6) | ND |

ND = Not Determined

TABLE 7b

Stability of Lyophilized Liposomal Vaccine
Formulation of Lysozyme (Lipo-Lyz (Lyo))

| Time | Stored at Temp (° C.) | Measured Lysozyme (mg/ml) Mean (±SD) | Particle diameter (nm) Mean (±SD) | Antibody titer (mg/ml) Mean (±SD) |
|---|---|---|---|---|
| t0 | N/A | 0.26 (±0.01)[a] | 667 (±113) | 306 (±207) |
| 13 months | 5 ± 3 | 0.27 (±0.03) | 647 (±14) | ND |
| 28 months | 22 ± 2 | 0.32 (±0.00) | 691 (±58) | 1,918 (+3,406) |

[a]Assumed to be unchanged after lyophilization.

Characterization of Antibody Response to Each Formulation by Indirect ELISA

FIG. 1 shows an exemplary immune response (450 nm absorbance) of the various formulations as compared at different dilutions of the sera (80,000, 160,000, and 320,000-fold). The amount of absorbance at 450 nm reflects the amount of antibody present in the sera.

Figure 2:
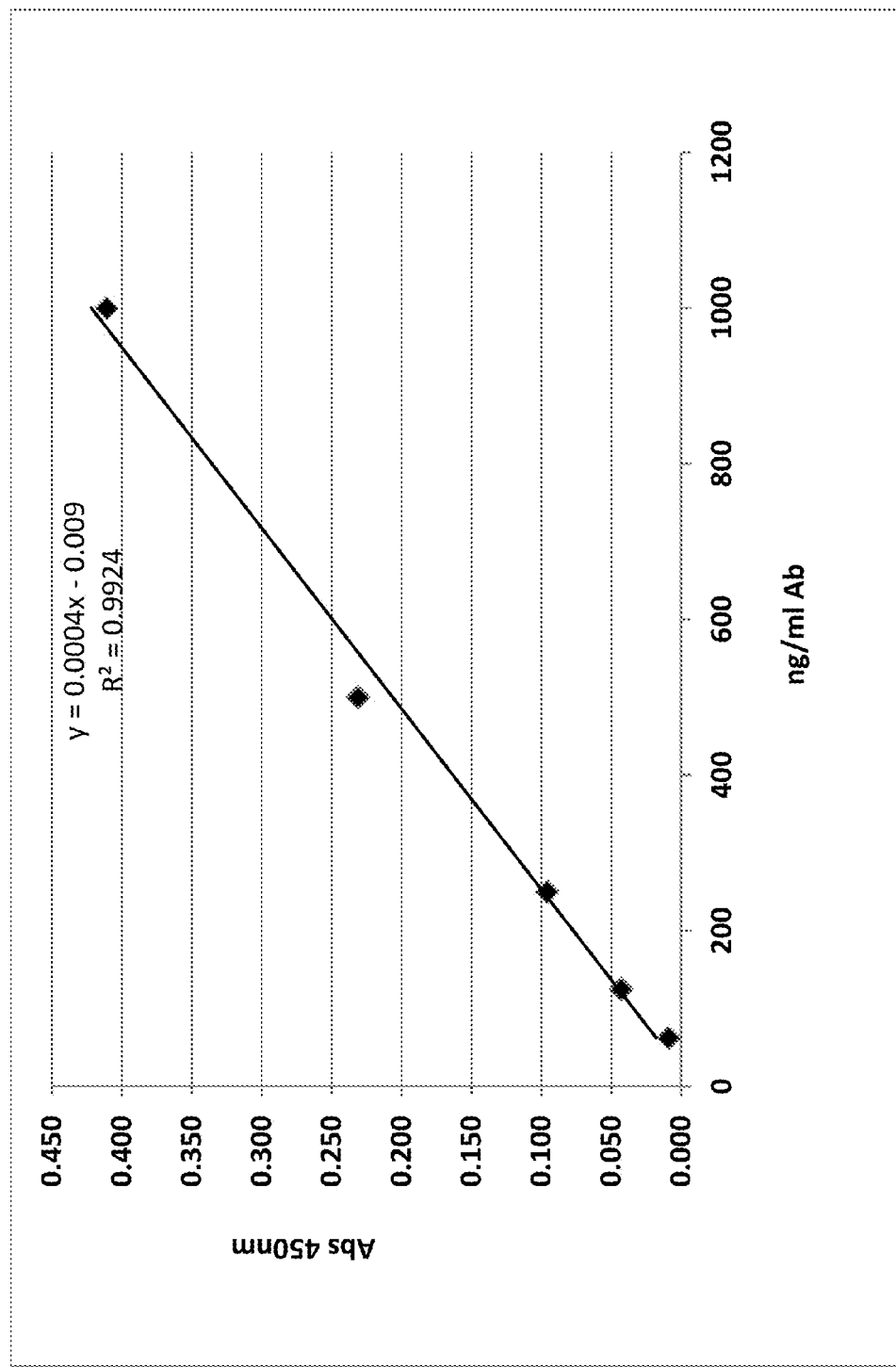
FIG. 2 shows an exemplary standard curve of mouse anti-lysozyme antibody.
Figure 3:
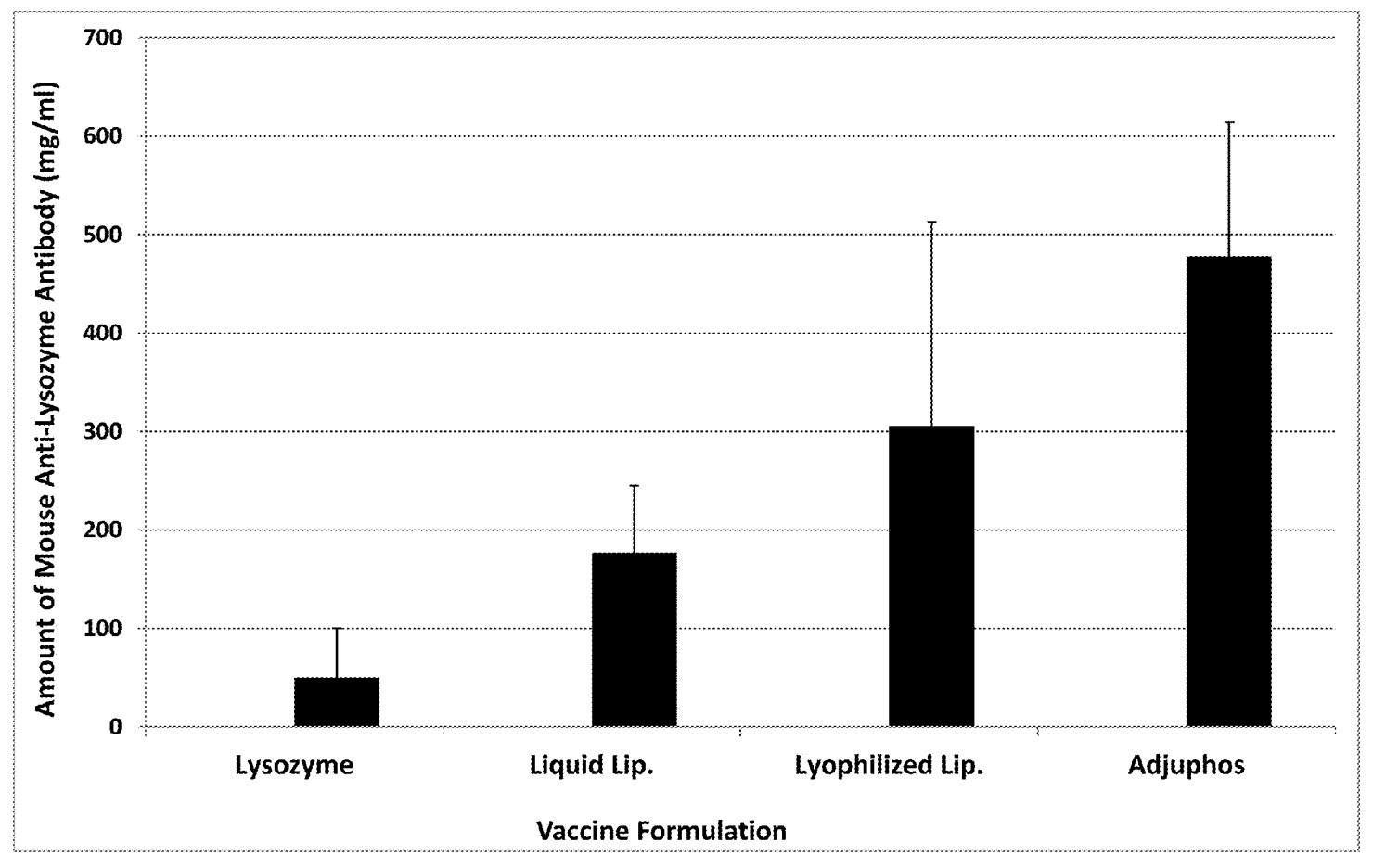

FIG. 2 shows an exemplary standard curve of mouse anti-lysozyme antibody, while FIG. 3 depicts an exemplary average amount of mouse anti-lysozyme antibody for a given formulation (mg/ml).

The amount of mouse anti-lysozyme antibody from the immune response of each of the four formulations was determined using a standard curve for purified mouse anti-lysozyme antibody (Raybiotech). A representative standard curve is shown (FIG. 2), with the standard curves being similar for all of the four ELISA plates.

The average quantified immune response to the lysozyme vaccines from each group of mice (n=4) and the corresponding standard deviations are shown (FIG. 3). The group of naive mice did not give any immune response as expected (negative control) and lysozyme without adjuvant had the lowest amount of antibodies induced.

The liquid liposomal vaccine induced approximately three times the amount of antibodies as the lysozyme without adjuvant. The lyophilized liposomes showed a six-fold increase in antibodies. The Adju-Phos® (Adju-Lyz) vaccine had the highest immune response, a nine-fold increase from the lysozyme alone. Characteristics of the various vaccines are summarized in Table 6.

A two-tail t-test performed to evaluate the significance between the lyophilized liposomal formulation and Adju-Phos® formulation, as well as the liquid and lyophilized liposomal formulations, gave p-values of 0.06 and 0.11, respectively. This showed that there was no significant difference between lyophilized liposomal formulation and Adju-Phos® formulation, as well as the liquid and lyophilized liposomal formulations at the 95% confidence limit.

The formulations, in order of increasing immunogenic response, are as follows:

Lysozyme formulation<liquid liposomal formulation<lyophilized liposomal formulation≃Adju-Phos® formulation.

The results show that all the vaccine formulations (Lipo-Lyz (Aq), Lipo-Lyz (Lyo) and Adju-Lyz (Aq)) were better than the control lysozyme (Lyz) solution, inducing a significant immune response in mice. The findings of this study clearly demonstrate that the freeze-stable liposomal vaccine can be as immunogenic as an aluminum-based vaccine. In addition, the freeze stable liposomal vaccine can be lyophilized into a stable, dry product that has the potential to become a room temperature stable vaccine.

Freeze-Stability of Vaccines

It is well-known that aluminum-based vaccines are freeze-sensitive (Wolff et al., "Development of a formulation protecting aluminum hydroxide adjuvanted vaccines during lyophilization", Proc. $6^{th}$ World Meeting Pharma. Biopharm. Pharma Tech., Barcelona, ES (2008)) and as further summarized herein (Table 1). According to aspects of the present invention, the liposomal vaccine compositions described herein were freeze-stable; they did not lose their immunogenicity despite multiple freeze-thaw cycles and, in the case of the freeze-dried formulation, freezing at −45° C. during lyophilization also failed to erode the immunogenicity of the claimed composition. Similarly, after freeze-drying, no negative attributes such as large aggregates or increase in liposome sizes were observed, as discussed below.

The Effect of Particle Size on Immune Response

Figure 4A:
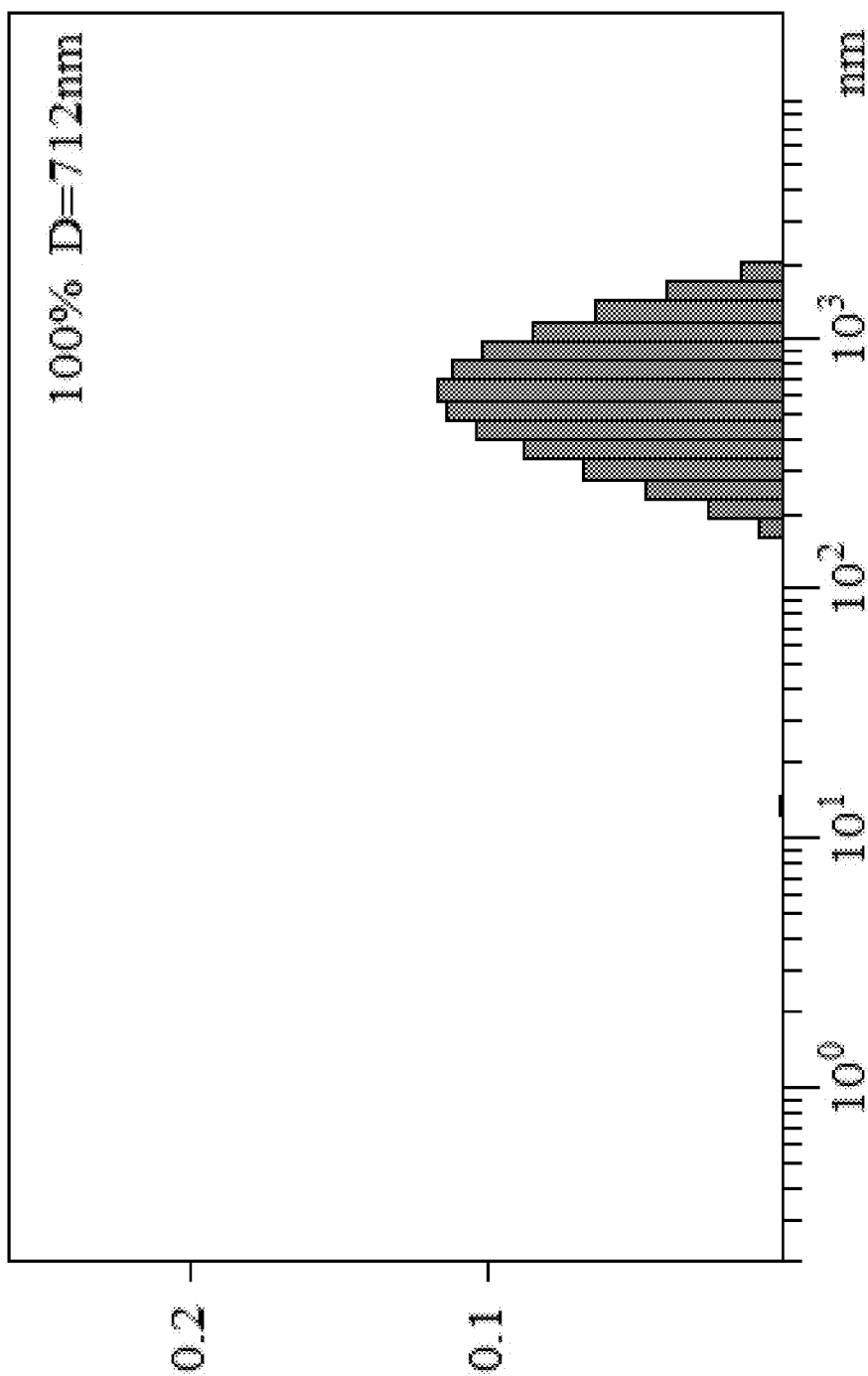
FIG. 4 shows the particle size distribution of liposomal vaccines across a variety of composition types, processing variations, time points and temperature variations. (a) Liquid liposome at t0; (b) liquid liposome at 13 months; (c) freeze-dried liposome (reconstituted) at t0; (d) freeze-dried liposome (reconstituted) after 28 months at room temperature; and (e) freeze-dried liposome (reconstituted) after 13 months at 5° C.).
Figure 4B:
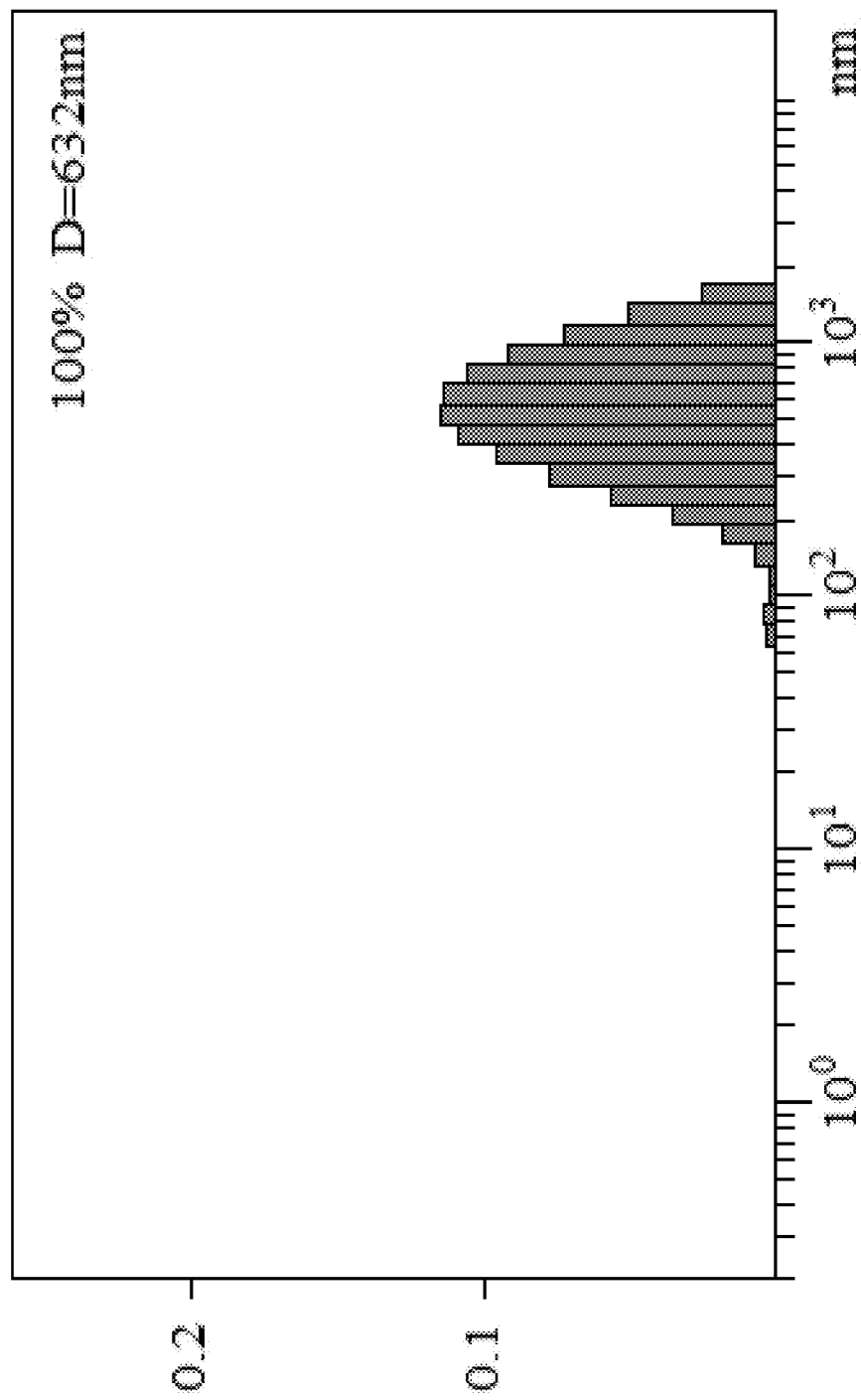
Figure 4C:
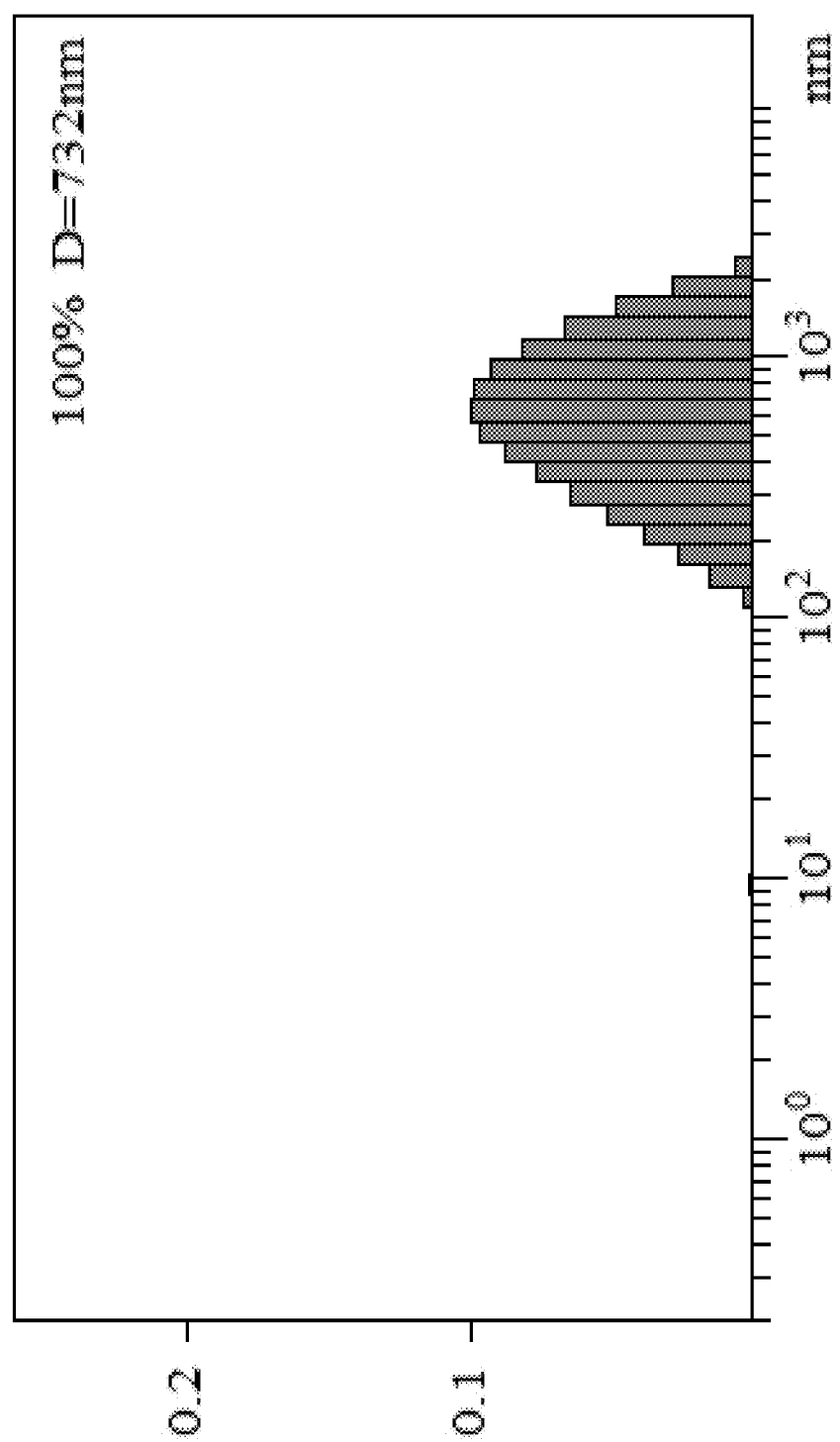
Figure 4D:
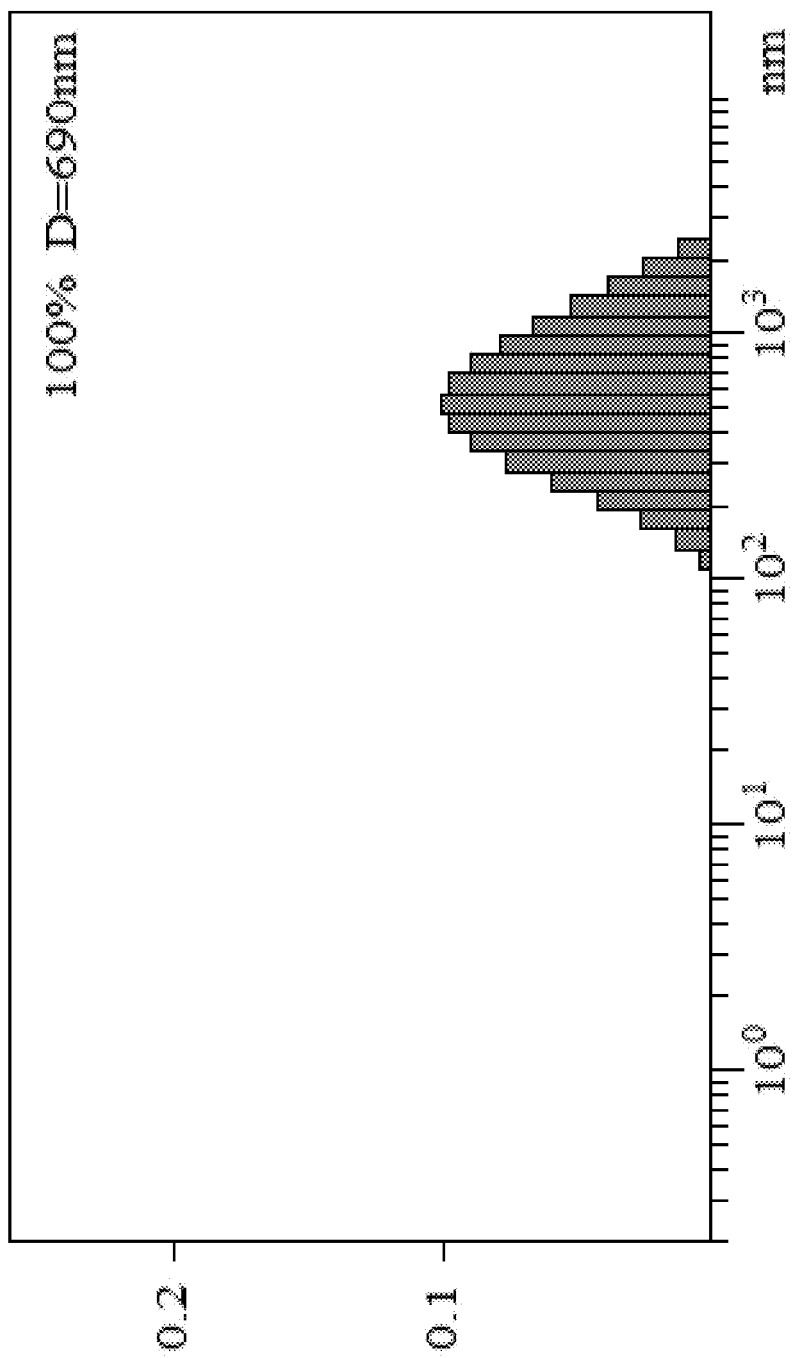
Figure 4E:
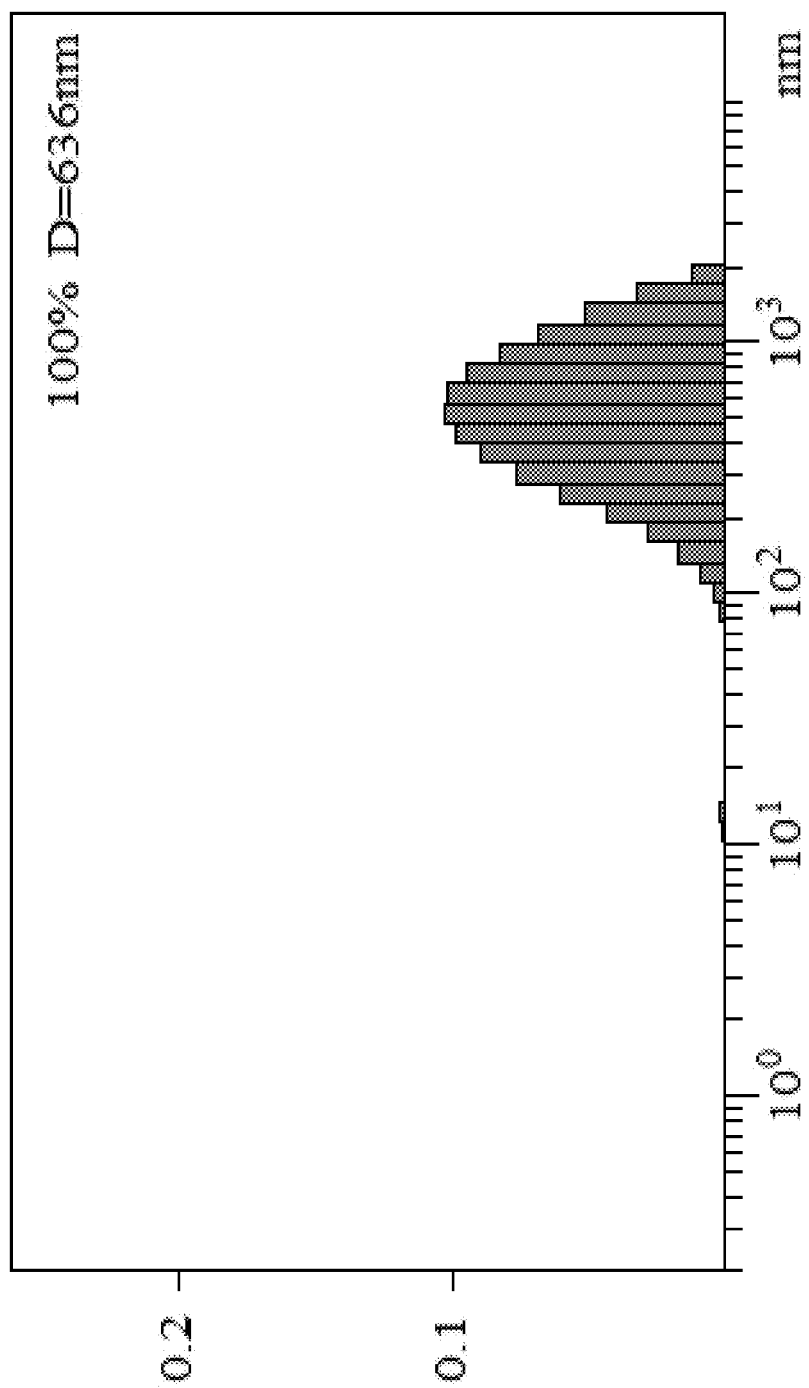

Liposome mean particle diameters before and after lyophilization remained relatively identical (Table 6) and representative particle size distribution by intensity were shown (FIG. 4a-e) at varying composition features and across different time points, including liquid liposome at t0 (FIG. 4a), liquid liposome at 13 months (FIG. 4b), freeze-dried liposomes (reconstituted) at t0 (FIG. 4c), freeze-dried liposome (reconstituted) after 28 months at room temperature (FIG. 4d) and freeze-dried liposome (reconstituted) after 13 months at 5° C. (FIG. 4e).

It is further evidence of the value of the compositions of the present invention, particularly in view of the longevity of the liposomal structural integrity under room temperature conditions over many months. Indeed, this suggests that the slight difference in immune response induced between the two formulations was not due to a change in particle size. This is also corroborated by observing that despite the large difference in particle size between liposomal formulations and the Adju-Phos® formulation, similar immune responses were induced. In fact, it has been shown that anti-lysozyme titers were independent of the particle size for vaccines adjuvanted with either aluminum hydroxide or aluminum phosphate and also unaffected by the level of antigen binding to the adjuvant.

Stability of Lyophilized Liposomes at Room Temperature

According to the methods and compositions of the present invention, as stated expressly herein at Table 7b, there were no changes in mean particle diameter of liposomes after 2 years in storage at room temperature. Similarly, there was no change noted in the average lysozyme concentration in the lyophilized liposomal lysozyme vaccine that was reconstituted after more than 2 years storage at room temperature. These results suggest that the formulation was stable at room temperature in regards to particle size and antigen concentration.

II. Liposomal Vaccine Composition with Tetanus Light Chain Antigen

Lipids used in this formulation include the following: dipalmitoyl phosphatidylcholine (DPPC), dioleoyl phosphatidylcholine (DOPC), cholesterol, and a negatively charged lipid dipalmitoyl phosphatidylglycerol (DPPG). These lipids were supplied from Avanti Lipids. Octadecylamine, which is the equivalent of stearylamine (SA), a positively charged lipid, was supplied from Fluka.

Recombinant light chain from tetanus toxin (TLC) 10 μg was supplied by List Biological Laboratory Inc, Cat. No. 650 A, lot 6503A1 and was used as the model antigen. TLC has a molecular weight of 50,000 Da, a pI of 5.06 and is a non-toxic protein. TLC is the smaller polypeptide chain of tetanus toxoid and retains the enzymatic activity encoded by the holotoxin.

Tween-20 (10% w/w Solution), Trehalose, lactose, HEPES, PBS, sodium citrate, citric acid, sodium hydroxide and Milli-Q® water comprised the remainder of the composition in solution.

A positively charged liposomal adjuvant system was made in a similar fashion as described in Example I, except with the lipid blend molar ratio of 40:25:20:15 containing DPPC:DOPC:cholesterol:SA. Recombinant tetanus light chain (TLC) was entrapped and/or associated with the lipid blend by hydration in the protein solution. The solution was subjected to three freeze-thaw cycles and extruded through 800 nm pore Nucleopore membranes. The free unassociated TLC was removed by dialysis and the liposomal TLC complex was diluted to around 120 ng/ml protein.

As a control, a non-adjuvant solution of just the TLC solution was injected into mice. All the solutions were totally dosed at 10 ng TLC per mouse (Table 8). One IM injection of 50 µl/mouse was administered into 5 mice per group and serum was collected following two weeks after the second booster injection of the test articles.

Immunogenicity to the tetanus toxoid was evaluated using the mouse anti-tetanus toxoid IgG ELISA kit that detects and quantifies tetanus toxoid-specific IgG in mouse serum of vaccinated or immunized animals (ELISA Kit Cat No. 930-130-TMG, Alpha Diagnostic International, San Antonio, Tex., USA).

The material for the ELISA consisted of the following: mouse anti-tetanus toxoid IgG ELISA was used for quantitative determination of anti-tetanus toxoid IgG in serum. This kit included tetanus toxoid coated strip plate (Part 930-111, lot 11045P6), anti-tetanus toxoid IgG calibrators (10 U/ml, 20 U/ml, 40 U/ml and 80 U/ml), mouse x-tetanus toxoid IgG (as positive control, part 930-132), low NSB sample diluent (Part TBTm), TMB substrate, and stop solution (part 80101, dilute sulfuric acid). Wash solution concentrate (Cat. WB-100), sample diluent concentrate (Cat. No. SD-20T) and anti-mouse IgG-HRP-conjugate concentrate (Part H-MsG-112b) were also utilized. The wash solution was diluted 100× in milliQ water prior to use. A working sample diluent was made by mixing 2.5 ml sample diluent with 47.5 ml Milli-Q® water.

Results from the mouse immunogenicity study are shown (FIGS. 5 and 6), where the average titers of mouse anti-tetanus toxoid IgG from 5 mice are compared among the formulations (FIG. 6) against the standard curve (FIG. 5).

The results clearly show that the cationic liposomes containing TLC in both the liquid formulation that had been freeze-thawed three times and the lyophilized formulation that had been frozen to −40° C. and lyophilized gave a significant immune response and generated IgG antibodies to tetanus toxoid as measured by ELISA (Table 12). The naïve and TLC solution without adjuvants did not give a significant immune response against the tetanus toxoid. Particle size was analyzed and specific sizes described in Table 11.

III. Lipid Blend Composition with Tetanus Light Chain as Antigen

In order to experimentally deduce preferred compositions and preparatory methods of different lipid blends, and their resultant immunogenicity, liposomal vaccine formulations were prepared and described, as indicated in Table 8.

TABLE 8

TLC Dosing and Total Lipid Content in Liposomal Vaccine Formulations

| Sample | ID | Booster shot | Inj/time point | Antigen conc (ug/mL) | Adjuvant conc. (mg/mL) | Vol. inj (ul) | Antigen/dose | Adjuvant/dose | Ratio (Adjuvant/protein) (ug/ug) | Total Antigen injected after 2 doses (ng) | Total lipid injected after 2 doses (ug) |
|---|---|---|---|---|---|---|---|---|---|---|---|
| Anionic liposomes (study 1) Aq | SP-318-2 | Y | 50 | 0.1 | 6 | 50 | 5 | 0.3 | 60,000 | 10 | 600 |
| Anionic liposomes (study 1) FD | SP-318-3 | Y | 50 | 0.1 | 6 | 50 | 5 | 0.3 | 60,000 | 10 | 600 |
| Cationic liposomes (study 1) Aq | SP-318-4 | Y | 50 | 0.1 | 6 | 50 | 5 | 0.3 | 60,000 | 10 | 600 |
| Catonic liposomes (study 1) FD | 5P-318-5 | Y | 50 | 0.1 | 6 | 50 | 5 | 0.3 | 60,000 | 10 | 600 |
| Anionic liposomes (study 2) Aq | 5P-329-2 | y | 100 ul (2 × 50) | 0.4 | 25 | 100 | 40 | 2.5 | 31,250 | 80 | 5000 |
| Anionic liposomes (study 2) FD | 5P-329-3 | y | 100 ul (2 × 50) | 0.4 | 25 | 100 | 40 | 2.5 | 31,250 | 80 | 5000 |
| Cationic liposomes (study 2) AQ | SP-329-4 | y | 100 ul (2 × 50) | 0.4 | 25 | 100 | 40 | 2.5 | 31,250 | 80 | 5000 |
| Cationic liposomes (Study 2) FD | SP-329-5 | y | 100 ul (2 × 50) | 0.4 | 25 | 100 | 40 | 2.5 | 31,250 | 80 | 5000 |

Preparation of Lipid Blend

In order to prepare the cationic liposomes, two vials were prepared, each with about 6.6 mg SA, 48.6 mg DPPC, and 12.7 mg cholesterol added to 1.6 ml of 20 mg/ml DOPC/chloroform (32 mg). The total amount of lipid in each vial was 100 mg.

Similarly, to prepare the anionic liposomes, two vials were prepared, each with about 43.5 mg DPPC, 16.6 mg DPPG, and 11.5 mg cholesterol in 1.45 ml DOPC/chloroform (29 mg). The total amount of lipid in each vial was 100 mg.

Since all the lipids failed to dissolve in chloroform, an 83% methanol/water solution was added to obtain a clear solution. The lipid blends were first dried in a 45° C. water bath under nitrogen gas, and then the residual solvent was removed under vacuum overnight, to ensure complete desiccation. Two lipid blend vials were used per study.

Preparation of 10 μg/ml TLC Stock Solution at pH 7.4 or pH 4.0 in 0.05% Tween A 0.05% Tween-20 solution was made by diluting 25 μl Tween-20 in 5 ml water. In Study 1, each vial of lyophilized recombinant Tetanus light chain (10 μg) was reconstituted with 1 ml 0.5% Tween-20 solution to obtain a 10 μg/ml tetanus solution in 20 mM HEPES (pH 7.4) and 1.25% lactose.

In Study 2, 0.05% Tween-20 solutions were made either in citrate buffer (pH 3.7) or in 20 mM HEPES (pH 7.4) with 1.25% lactose. 1 ml of each solution was used for reconstitution of one TLC vial.

Hydration of Lipid Blend

Cationic and anionic lipid blends were then hydrated with 0.9 ml of the TLC stock solutions. In Study 1, both cationic and anionic liposomes were made at pH 7.4, whereas in Study 2, the liposomes were made at pH 7.4 and 4.0, respectively. The mixtures were stirred on a magnetic stirrer for 15 minutes and sonicated for 10 seconds until the lipids were totally hydrated into a milky homogenous solution.

Multiple Freeze-Thaw Cycles

In order to improve the entrapping efficacy, the liposome solutions were freeze-thawed three times using an acetone-ice bath and a warm-water bath. The solutions were then diluted to a concentration of 6 μg/ml TLC in Study 1 and 5 μg/ml in Study 2.

Extrusion

To reduce the size of liposomes and to obtain a more homogenous particle distribution, each liposome solution was extruded ten times through two 800 nm polycarbonate filters (Nucleopore) in a 10 ml Extruder (Northern Lipids) at 50 psi using nitrogen gas.

Dialysis

In order to separate the free TLC from the incorporated TLC, the liposome solutions were dialyzed through Float-A-Lyzer G2 (Spectrum labs) with 300,000 Da (Study 1) or 1,000 kDa (Study 2) molecular weight cut off (MWCO) membranes against PBS buffer (pH 7.4) overnight (Study 1).

In Study 2, 1.5 ml of liposomes were dialyzed against either 1.25% lactose, 20 mM citrate buffer, pH 4.0 (anionic liposomes) or 500 ml of 1.25% lactose, 20 mM HEPES (cationic liposomes) overnight (18 hrs).

300,000 Da MWCO membranes were used because liposomes would be unable to pass, but the free TLC, which is smaller (50,000 Daltons), would be able to pass through the membrane.

Filling

After dialysis each solution was transferred to a tube in a sterile hood.

A solution containing 100 ml 10 wt % trehalose in 10 mM Hepes buffer was prepared by dissolving 238.3 mg HEPES and 10 g trehalose in 90 g water until final weight of solution reached 100 g (pH of the buffer was measured to be 7.05) and sterile filtered using a 0.22 micron filtration flask.

4.5 ml 10% trehalose in a 10 mM Hepes solution was added to 0.5 ml of each liposome solution. Assuming a 20% entrapment efficiency for TLC in liposomes, the concentration of TLC should be about 0.1 μg/ml for cationic liposomes and anionic liposomes in the Study 1, and 0.4 μg/ml in the Study 2.

Freeze-Drying

For each formulation, five of the vials were freeze-dried in a Vertis Freeze-dryer (Vertis Genesis 12XL) by first freezing the solution at −45° C. and then subliming the ice at −30° C. and −40° C. under high vacuum in Study 1 and 2, respectively. Secondary drying was performed at 25° C. shelf temperature to remove any residual water from the cake. A summary of drying conditions are described in Table 9.

TABLE 9

Freeze-Drying Conditions[a]

| Freeze-drying steps | Temperature | Time (Minutes) | Ramp/ Hold | Pressure |
|---|---|---|---|---|
| Freezing | +5 | 15 | H | 1 ATM |
|  | −45 | 60 (120) | R | 1 ATM |
|  | −45 | 60 (240) | H | 1 ATM |
| Primary Drying | −45 | 60 | H | 150 (100) mTorr |
|  | −30 (−40) | 30 | R | 150 (100) mTorr |
|  | −30 (−40) | 1200 | H | 150 (100) mTorr |
| Secondary Drying | +25 | 240 | R | 150 (100) mTorr |
|  | +25 | 600 | H | 150 (100) mTorr |

[a]The parenthetical values are parameters used in Study 2.

Preparation of Diluents

Diluents (reconstitution solutions for the freeze-dried vaccines) were also prepared for the lyophilized samples by filling 1 ml of WFI into five vials.

Preparation of TLC without Adjuvant

In Study 2, 0.15 ml of TLC solution (10 μl in 0.05% Tween-20) was diluted in 2.5 ml HEPES, 10% trehalose, 0.05% Tween-20 (pH 7.4) to obtain a 0.6 μg/ml TLC solution.

Mice Immunization 50 and 100 μl (2×50 μl) of each formulation was injected IM in the shoulder of five female CD-1 mice (Charles River, Hollister Calif.) in Study 1 and 2, respectively. A booster shot was administered on day 14. Mice were tested in groups of five. 5 naïve mice were used as negative control and did not receive any injections. All of the animals were observed immediately after dosing and daily thereafter. On Day 28, serum was collected from the immunized mice as well as the control group. All animal testing was conducted according to an approved Animal Care and Use Protocol (ACUP). The animal studies were carried out in an animal facility that is fully accredited by the Association for Assessment and Accreditation of Laboratory Animal Care International.

Indirect ELISA Methods and Results

Immunogenicity to the tetanus toxoid was evaluated using a mouse anti-tetanus toxoid IgG ELISA kit that detects and quantifies tetanus toxoid-specific IgG in mouse serum of vaccinated or immunized animals (ELISA Kit Cat No. 930-130-TMG, Alpha Diagnostic International, San Antonio, Tex., USA).

The mouse sera was diluted (100:900 μl) in the working sample diluent (10×). Then each sera was diluted from 1:10 to 1:100 in LNSB buffer (10×).

Each well of a 96-well polystyrene microtiter plate (Alpha Diagnostics) was incubated with 200 μl wash buffer for 5 min. The wells were then rinsed and 100 μl of each diluted sample was added. The plate then incubated for one hour on an orbital shaker (VWR) at 150 rpm. The plate was removed and washed four times using washing buffer. 100 μl HRP-conjugated IgG Anti-Mouse antibody was diluted in 9900 μl working solution diluent. 100 μl of the diluted solution was subsequently added to each well and incubated for 30 min. The wells were then washed again five times and 100 μl TMB substrate was added to each well. The wells were incubated in the dark for 15 min to allow for the reaction and color change to take place. When the color in the wells turned blue, 100 μl stop solution was added to each well.

Absorbance of each well was measured at 450 nm (and also at 630 nm to normalize for well background), using a Spectromax® 190 microplate reader (Molecular Devices). Two duplicate readings were obtained per sample at each wavelength. The absorbance at 630 nm were subtracted from the corresponding values at 450 nm to reflect the amount of antibody in the serum at each dilution. The mean of two duplicate readings were calculated for each sample.

A standard curve was plotted using the absorbance values for the standards with known mouse anti-tetanus toxoid antibodies at 10 U/ml, 20 U/ml, 40 U/ml and 80 U/ml. Mouse anti-tetanus toxoid antibody titers were calculated from absorbance readings that fell on the standard curve for the mouse anti-tetanus toxoid standards and corrected for dilution factors (the mouse sera was diluted one hundred fold in all cases, except in cases of mice immunized with cationic liposomes. The sera of mice immunized with liquid and lyophilized cationic liposomes (TLC 0.4 µg/ml (Study 2)) were diluted totally one thousand fold and five hundred fold, respectively).

The mean and standard deviations of the antibody titers for each formulation were calculated. The mean values of antibody titers for 5 mice were calculated for all samples. The mean values obtained for each sample was subtracted from those obtained for naïve mice. Two-sample, one-tailed t-Tests were performed for the mean antibody titers of the liquid and lyophilized anionic and cationic liposomes (Study 2) to see whether lyophilization induced a significant difference in immunogenicity of the formulations. An alpha level of 0.05 was used. A p-value was calculated. If the p<alpha, the difference in the immunogenicity of the formulations before and after lyophilization would be significant.

Particle Size Characterization Using Dynamic Light Scattering (DLS)

50 µl of each liposomal vaccine was diluted 40-60 times and analyzed on a Precision Detector DLS instrument (PD2000DLSplus and PDDLS/CoolBatch 90T) using quartz cuvettes (Precision Detectors). Measurements were done at 20° C. using a refractive index of 1.3330 and a viscosity of 0.01002 Poise. Sample time was 15 µsec and 3 sec run duration with a total of 60 accumulations per measurement. Data was analyzed using Precision Deconvolve software. Each sample was analyzed in triplicate. A smoothing parameter of 20 was applied. The mean hydrodynamic diameters by intensity and standard deviations (SD) were calculated (n=3).

Results from Study 1

In Study 1, the particle size characterization of liposomal vaccines with 0.1 µg/rat TLC was analyzed. Representative particle size distribution by intensity were shown (FIG. 7a-d), with mean particle diameters (n=3) and standard deviations listed in Table 10.

TABLE 10

Particle Size Data[a] for Liposomal Vaccine with 0.1 µg/ml TLC (Study 1)

| Samples ID | Formulation | Particle Diameter (nm) Mean ± SD |
|---|---|---|
| SP-318-2 | Liquid anionic liposomes | 521 ± 37 |
| SP-318-3 | Lyophilized anionic liposomes | 357 ± 12 |
| SP-318-4 | Liquid cationic liposomes | 313 ± 8 |
| SP-318-5 | Lyophilized cationic liposomes | 349 ± 25 |

[a]These data are obtained from particle size distribution by intensity using smoothness 20 (n = 3).

Characterization of Antibody Response by Indirect ELISA for Liposomes with 0.1 µg/ml TLC (Study 1)

The amount of mouse anti-tetanus antibody from the immune response of each of the formulations was determined using a standard curve (FIG. 5) generated from a purified preparation of mouse anti-tetanus antibody.

Figure 8:
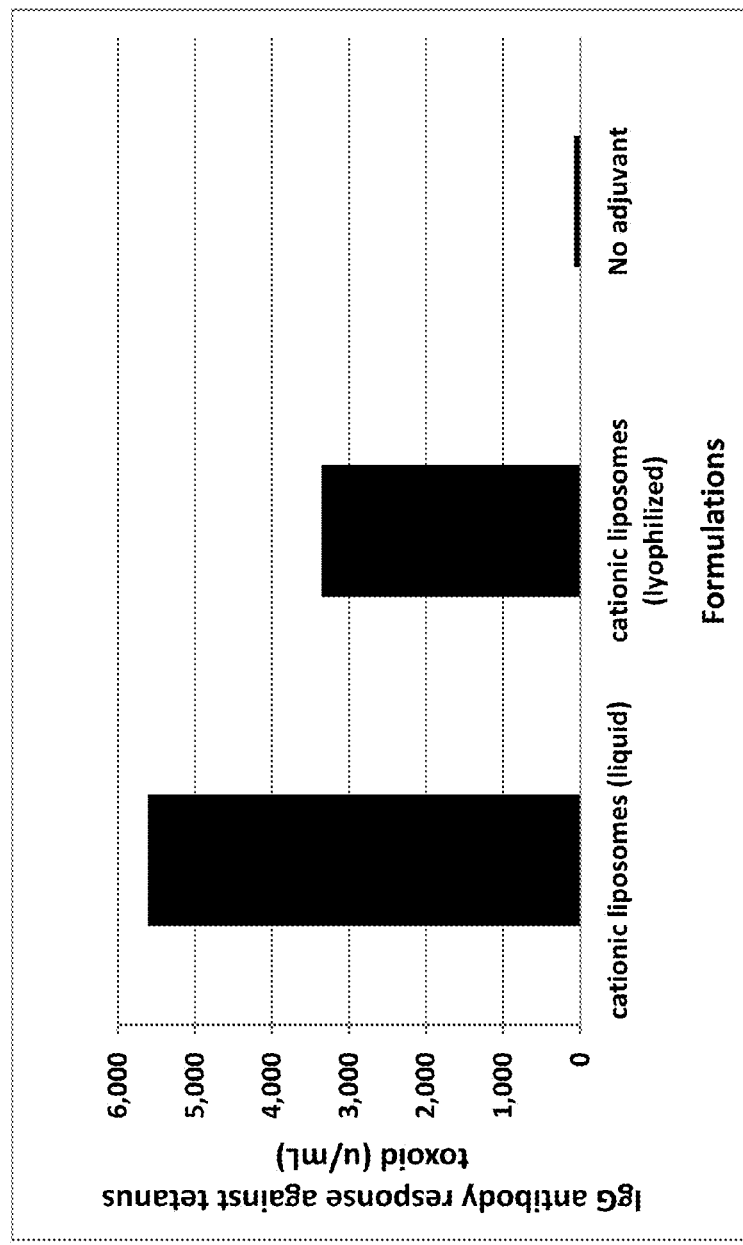
FIG. 8 shows the average amount of mouse anti-tetanus antibody for cationic liposomes with 0.1 µg/ml TLC. These results are from Study 1.
Figure 9A:
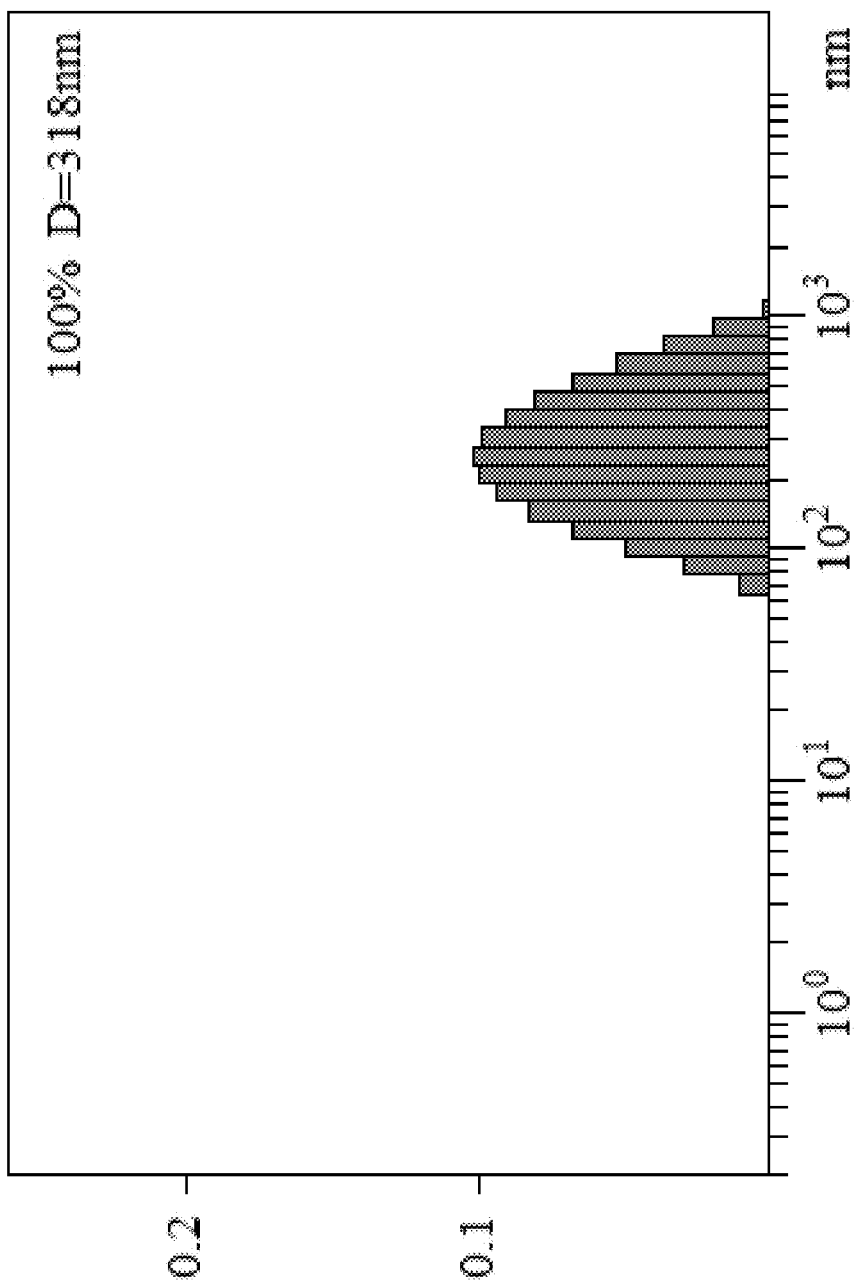
FIG. 9 shows the particle size distribution of liposomal vaccines, before and after freeze-drying, with smoothness 20 applied. These results are from Study 2. (a) Liquid anionic liposomal vaccine −0.4 µg/ml TLC, (Formulation 2; SP-329-2); (b) Lyophilized anionic liposomal vaccine −0.4 µg/ml TLC, (Formulation 3; SP-329-3); (c) Liquid cationic liposomal vaccine −0.4 µg/ml TLC, (Formulation 4; SP-329-4); and (d) Lyophilized cationic liposomal vaccine −0.4 µg/ml TLC, (Formulation 5; SP-329-5).
Figure 9B:
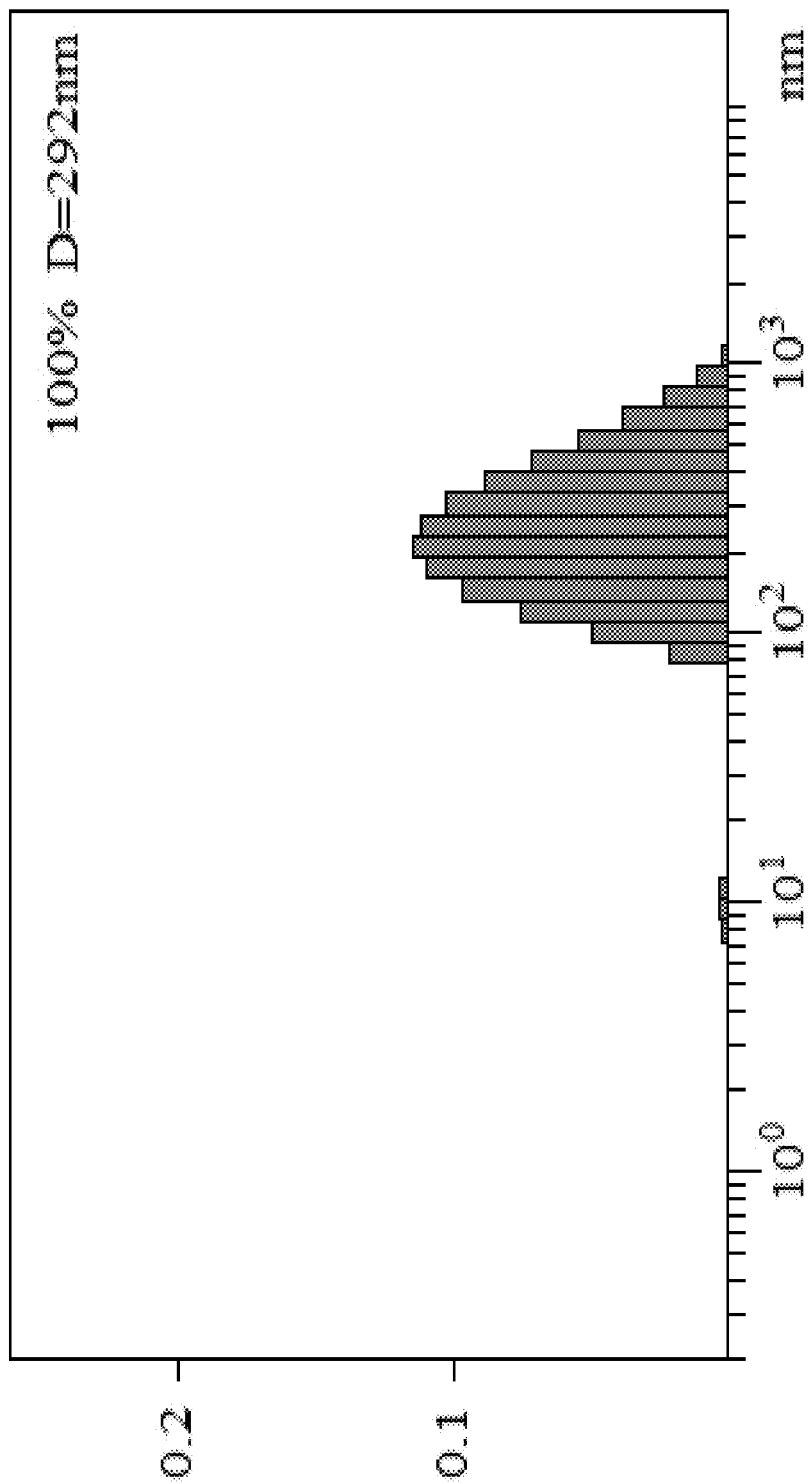
Figure 9C:
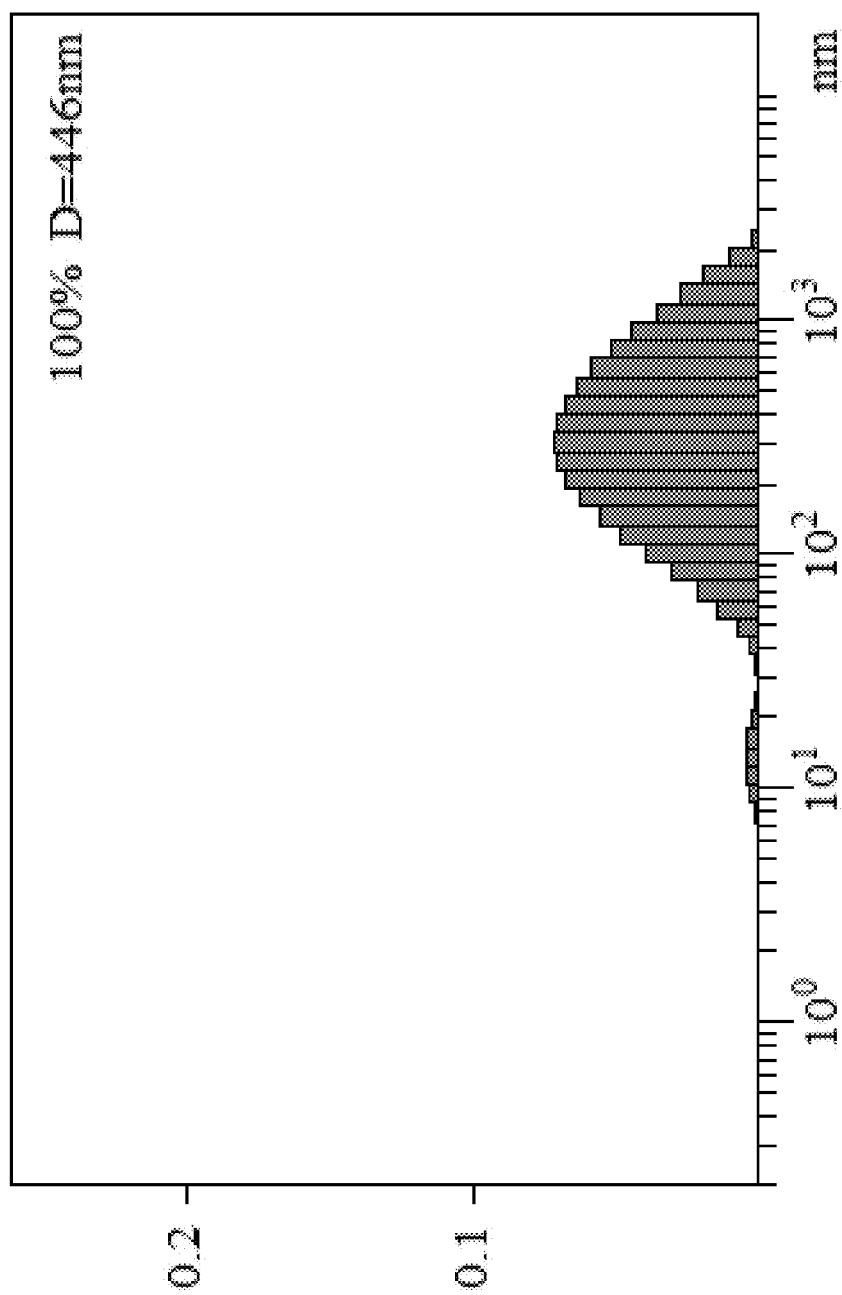
Figure 9D:
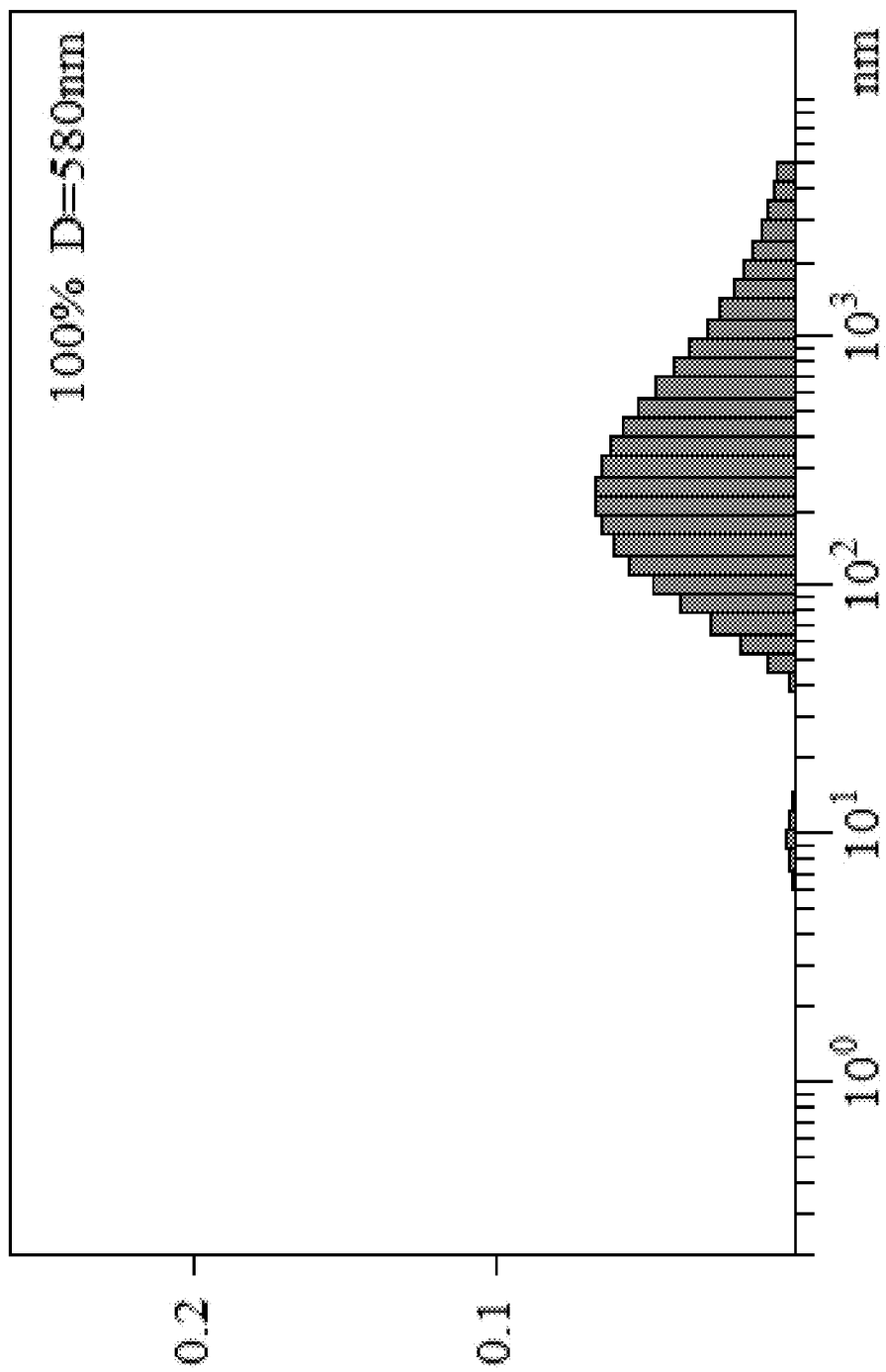

The average quantified immune response to the tetanus vaccines from each group of mice and the standard deviations are shown in Table 11. The average immune response for cationic liposomes-TLC (0.1 µg/ml) was also examined (FIG. 8) compared to a no adjuvant control.

Anionic liposomes did not show a significant immune response with tetanus at the dose used (50 µl of 0.12 µg/ml at t=0 and 14 days, i.e. 6 ng TLC and 0.3 mg lipid per injection). Cationic liposomes induced 4-6 times more antibody titers against tetanus toxoid than TLC without adjuvant (Table 11).

TABLE 11

Figure 5:
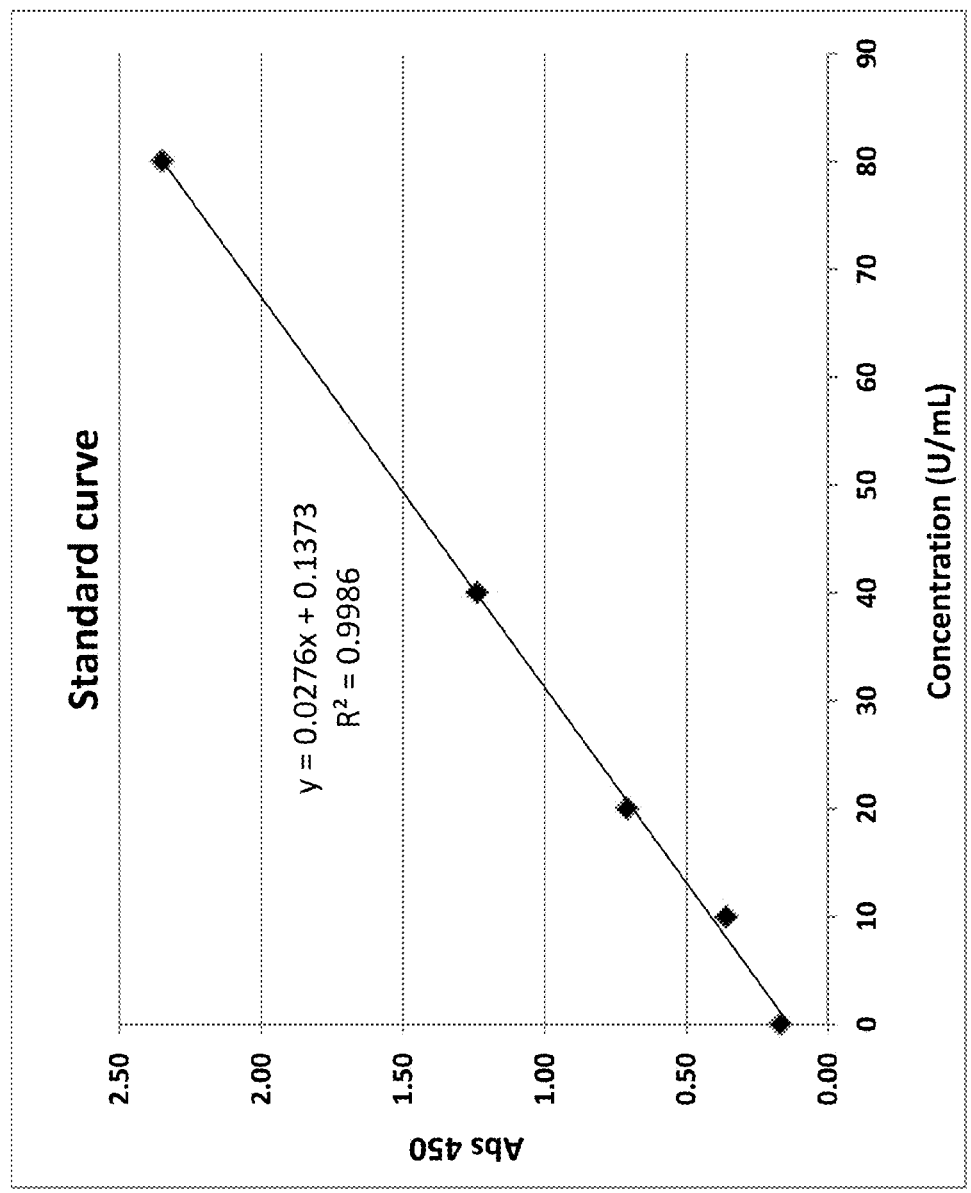
FIG. 5 depicts an exemplary average amount of mouse anti-tetanus toxoid antibody for different formulations ($Abs_{450}$).
Figure 7A:
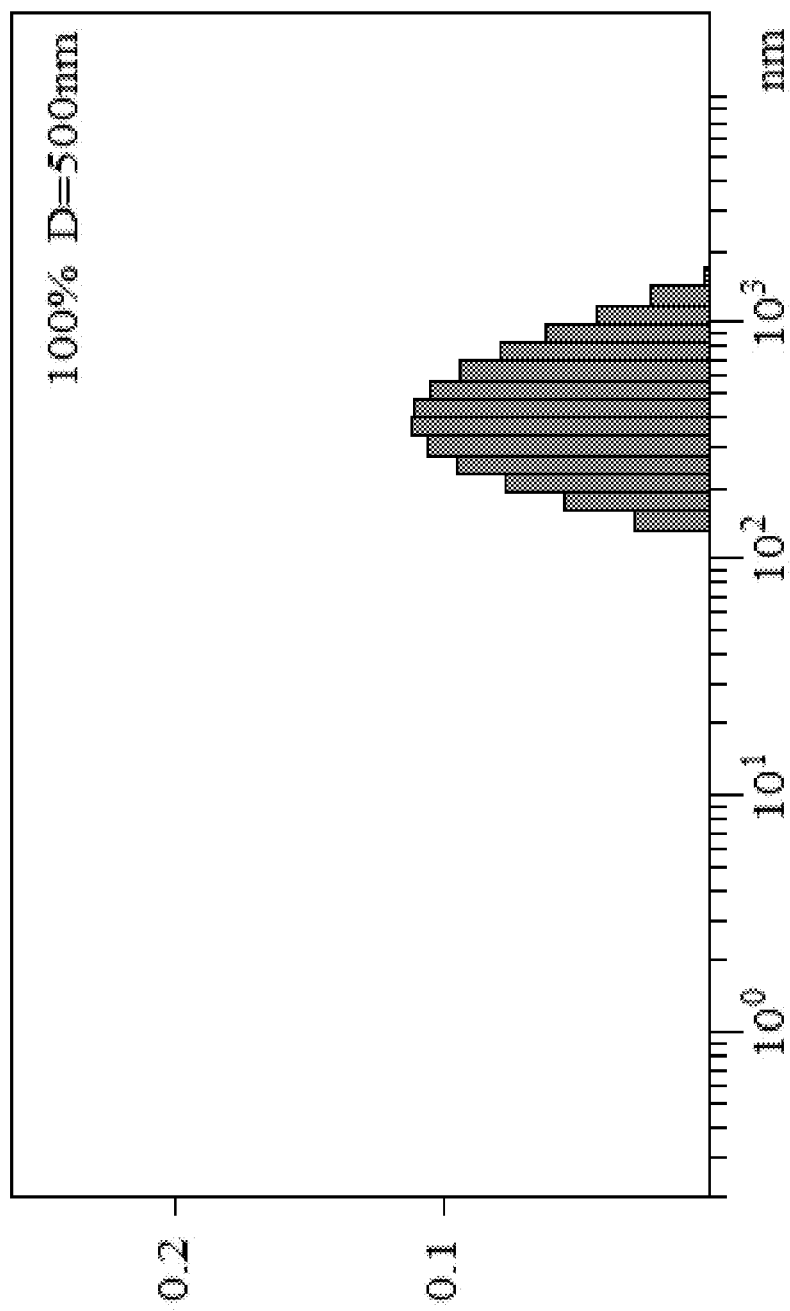
FIG. 7 depicts the particle size distribution of liposomal vaccines with 0.1 µg/ml TLC by DLS (before and after freeze-drying; smoothness 20 applied). These results are from Study 1. (a) Liquid anionic liposomal vaccine −0.1 µg/ml TLC, (Formulation 2; SP-318-2); (b) Lyophilized anionic liposomal vaccine −0.1 µg/ml TLC, (Formulation 3; SP-318-3); (c) Liquid cationic liposomal vaccine −0.1 µg/ml TLC, (Formulation 4; SP-318-4); (d) Lyophilized cationic liposomal vaccine −0.1 µg/ml TLC, (Formulation 5; SP-318-5).
Figure 7B:
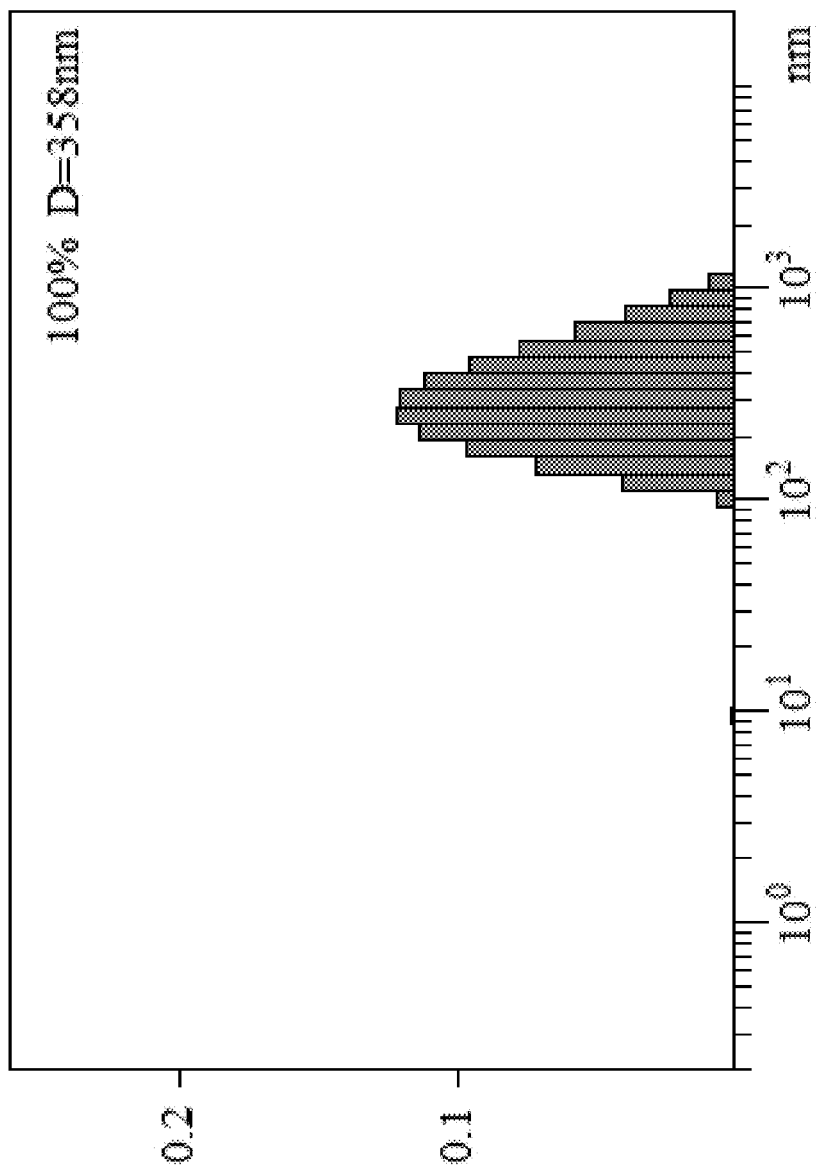
Figure 7C:
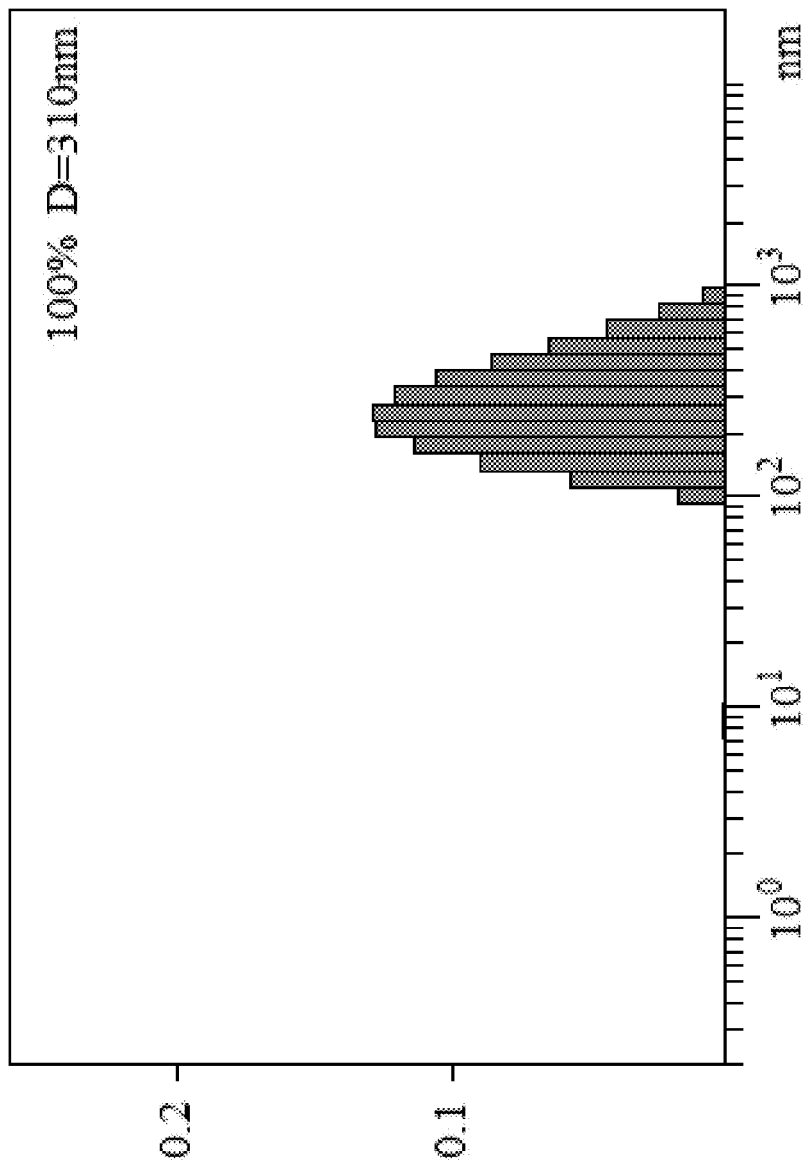
Figure 7D:
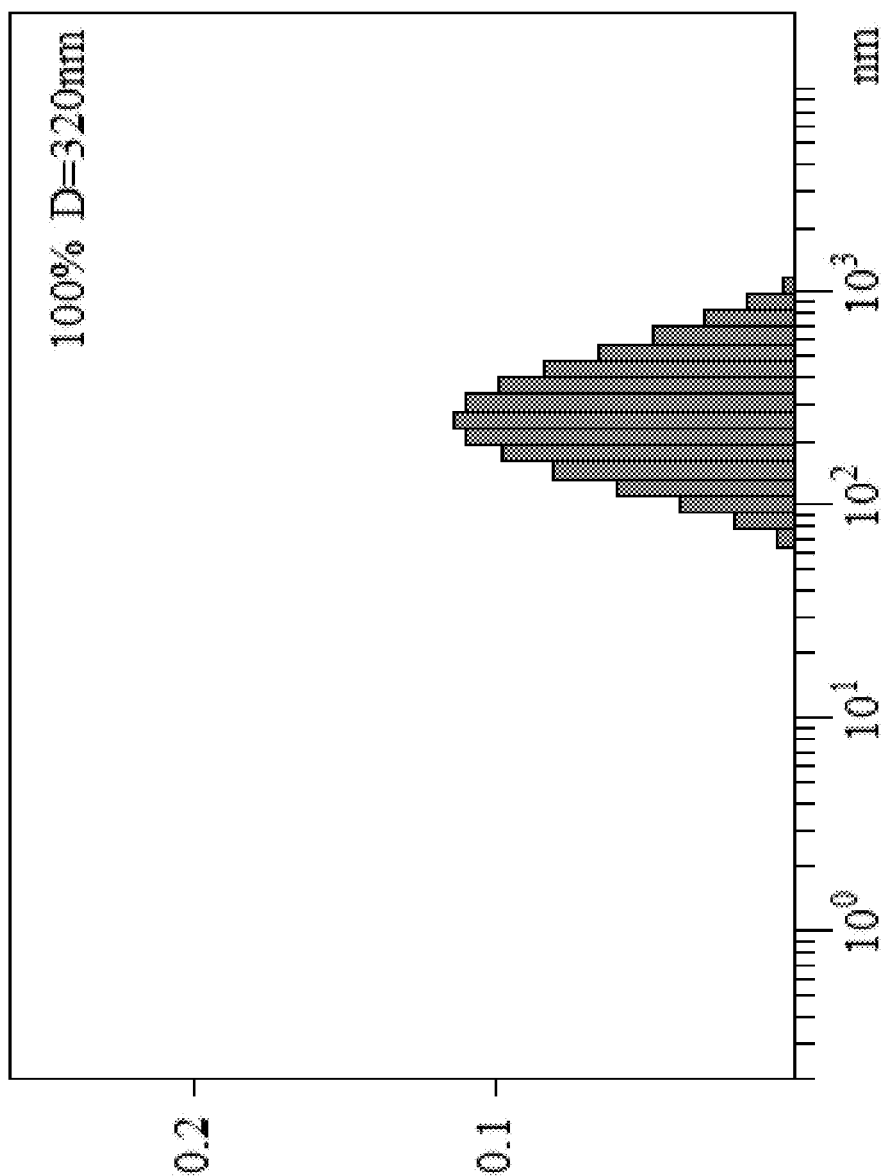

Average antibody response/formulation calculated from standard curve (FIG. 5)

| Sample ID | Formulation | Antibody response[a] (U/mL) | Particle Diameter[b] (nm) Mean ± SD |
|---|---|---|---|
| SP-318-6 | No adjuvant | 871 ± 1451 | — |
| SP-318-2 | Anionic liposome (liquid) | 82 ± 271 | 521 ± 37 |
| SP-318-3 | Anionic liposome (FD) | 1,183 ± 1,655 | 357 ± 12 |
| SP-318-4 | Cationic liposome (liquid) | 5,605 ± 6,399 | 313 ± 8 |
| SP-318-5 | Cationic liposome (FD) | 3,358 ± 3,395 | 349 ± 25 |

[a]These values are already corrected for the amount obtained for naïve mice (73 ± 126).
[b]These data are obtained from particle size distribution by intensity using smoothness 20 (n = 3).

Results from Study 2

The particle size analysis results for Study 2 are presented (FIG. 9a-d) and Table 12, with no significant change in the mean particle diameter of liposomes observed by DLS before and after freeze-drying. The results show that the mean particle diameter of anionic liposomes were more or less unchanged after freeze drying.

The mean particle diameter of cationic liposomes had increased slightly from 462 (±37) to 512 (±106) nm after freeze drying. This increase in particle size did not have any significant impact on the immune response obtained in mice (Tables 12 and 13).

TABLE 12

Data Summary for Immune Responses and Particle Sizes of the Liposomal Formulations with 0.4 mg/ml TLC (Study 2) (n = 5/formulation)

| Sample | Vaccine | Particle Diameter[b] (nm) Mean ± SD | Mouse Anti-Tetanus Toxoid IgG[a] (U/mL) Mean ± SD |
|---|---|---|---|
| SP-329-2 | Anionic liposomes-TLC (Aq) | 311 ± 8 | 7,080 ± 8,916 |
| SP-329-3 | Anionic liposomes-TLC (FD) | 315 ± 24 | 3,621 ± 5,525 |
| SP-329-4 | Cationic liposomes-TLC (Aq) | 462 ± 37 | 30,633 ± 40,697 |
| SP-329-5 | Cationic liposomes-TLC (FD) | 512 ± 106 | 34,140 ± 44,228 |
| SP-329-6 | TLC | ND | 1,316 ± 1,741 |

[a]In these values, the response obtained for naïve mice has already been subtracted.
[b]These data are obtained from particle size distribution by intensity using smoothness 20 (n = 3).

Characterization of Antibody Response by Indirect ELISA for Liposomes with 0.4 µg/ml TLC (Study 2)

Figure 10:
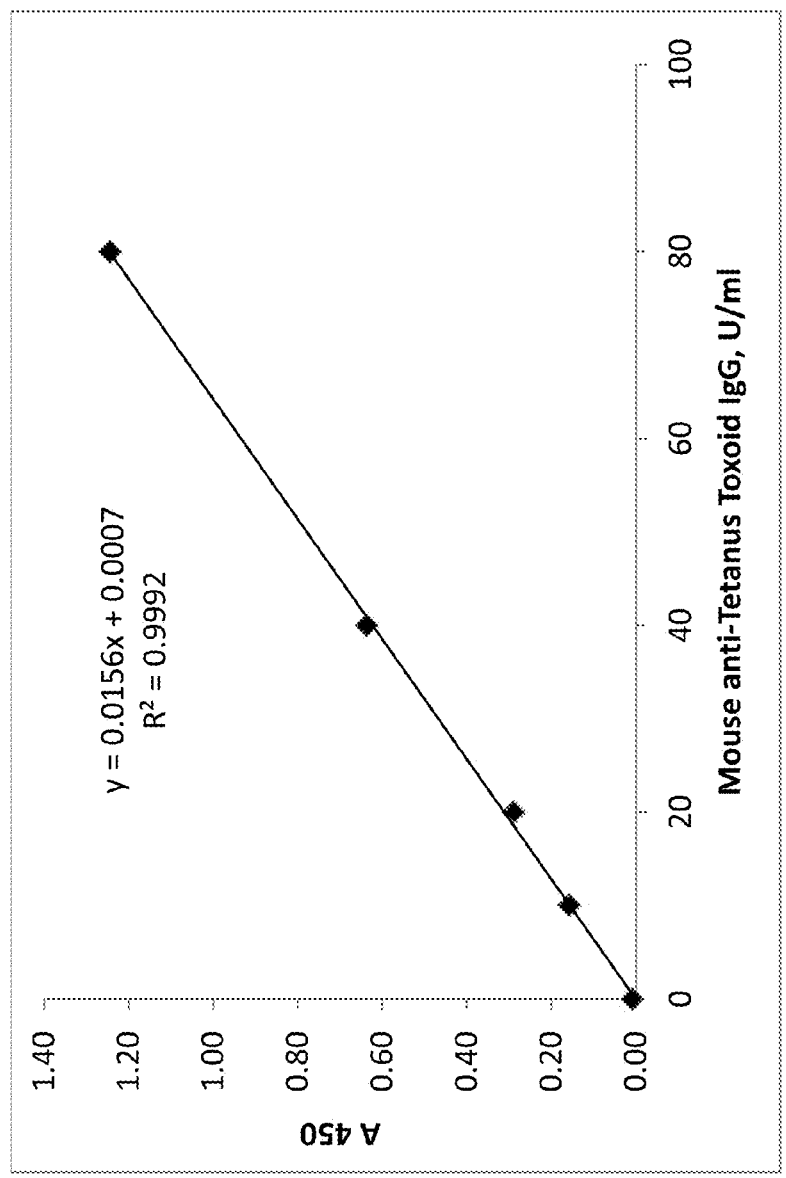
FIG. 10 shows a standard curve of mouse anti-tetanus antibodies obtained from Study 2.

The amount of mouse anti-tetanus antibody from the immune response of each of the formulations was determined using a standard curve (FIG. 10) generated from a purified preparation of mouse anti-tetanus antibody. The average quantified immune response to the tetanus vaccines from each group of mice and the standard deviations were calculated (FIG. 11) and summarized (Table 12). Average amounts of mouse anti-tetanus antibody for cationic liposomes with TLC (0.4 µg/ml) in study 2 are compared to TLC without adjuvant in FIG. 8.

Figure 11:
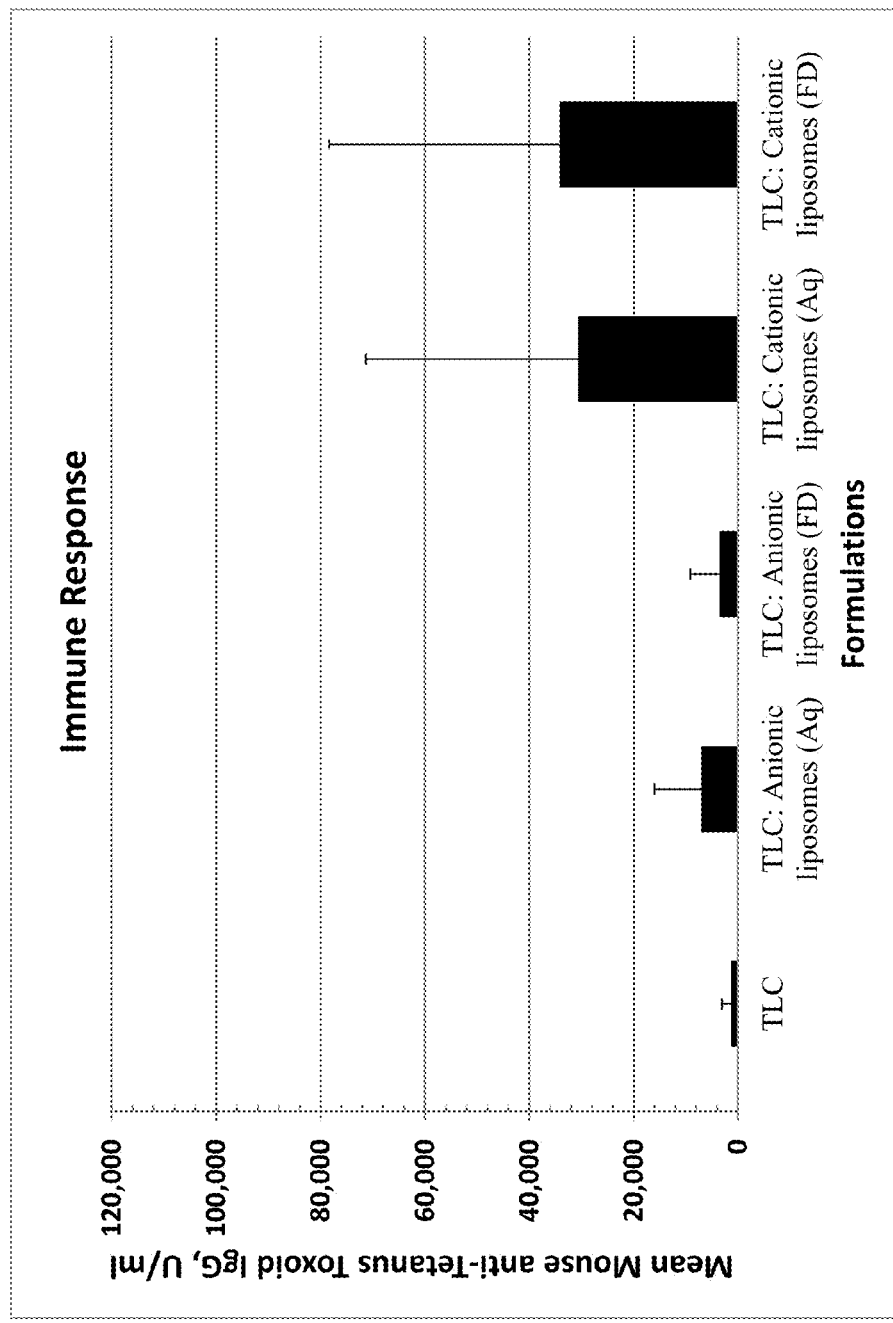
FIG. 11 shows the average amount of mouse anti-tetanus antibody for each formulation (U/ml) in Study 2. The bars show the standard deviations.

As indicated, TLC alone had a very low amount of antibodies induced (FIG. 11; Table 12). The liquid and lyophilized anionic liposomes induced approximately five and three times as many antibodies, respectively, as the TLC alone. The liquid and lyophilized cationic liposomes showed almost a forty- and fifty-fold increase in antibodies, respectively.

The results reveal that there is a significant difference between the cationic and anionic liposome formulations, with the cationic liposomes inducing a much stronger immune response. The liposomal vaccines retained their immunogenic activity after multiple freeze-thaws and also after freeze-drying.

The results reveal that there is a significant difference between the cationic and anionic liposome formulations, with the cationic liposomes inducing a much stronger immune response. Two-sample, one-tailed t-Tests were performed for the immune response obtained for liquid and lyophilized anionic and cationic liposomes to see whether lyophilization induced a significant difference in immunogenicity of the formulations. An alpha level of 0.05 was used. For the anionic formulations, a p-value of 0.243 was obtained, and for the cationic formulations a p-value of p=0.450 was obtained, with all results summarized at Table 13. Since alpha<p in both cases, it cannot be concluded that there was a significant difference in the formulation after lyophilization in either case.

TABLE 13

Parameters for the T-Test (Study 2)

| TLC-Anionic liposomes | | TLC-Cationic liposomes | |
|---|---|---|---|
| Liquid | Freeze-dried (FD) | Liquid | Freeze-dried (FD) |
| X = 7,080 | X = 3,621 | X = 30,633 | X = 34,140 |
| Sx = 8,916 | Sx = 5,525 | Sx = 40,697 | Sx = 44,228 |
| n = 5 | n = 5 | n = 5 | n = 5 |
| Ha: Liq > FD, t = 0.7374, df = 6.68, p = 0.243 | | Ha: Liq < FD, t = −0.1305, df = 7.945 p = 0.450 | |

Figure 12:
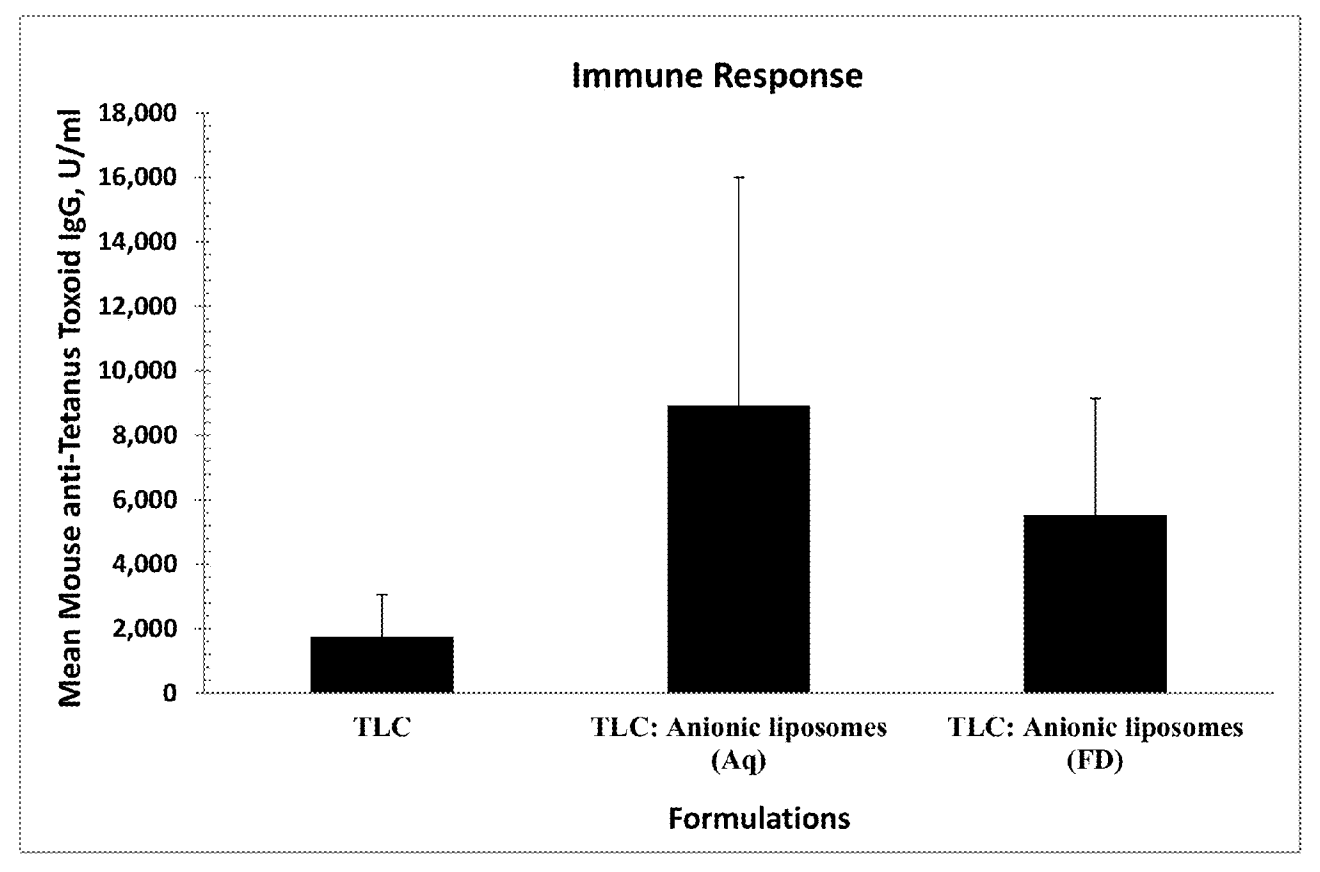

The mean particle size for cationic and anionic liposomes were relatively constant before and after freeze-drying (Table 12). There was a slight increase in mean particle size for the cationic liposomes after freeze-drying. According to statistical analysis this increase in particle size did not significantly affect the immune response of the vaccine formulation. Average amounts of mouse anti-tetanus antibody for anionic liposomes with TLC (0.4 µg/ml), both liquid and freeze-dried, were compared against TLC without adjuvant (FIG. 12).

IV. Comparison of Studies 1 and 2

The results obtained for the studies above are plotted as a function of lipid adjuvant or TLC in the dose received by mice (FIGS. 13-15).

Figure 13A:
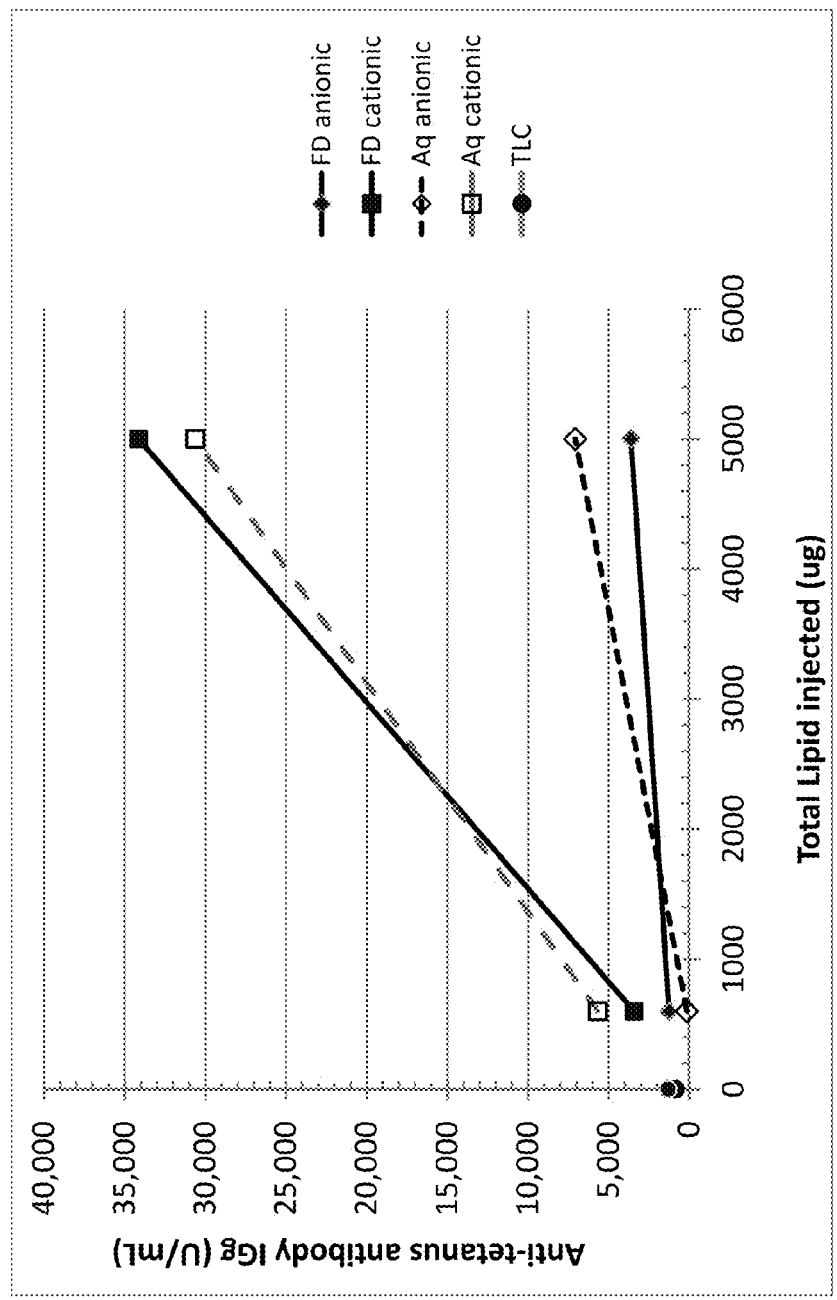
FIG. 13a shows the dose dependence and overall levels of anti-tetanus antibodies raised for the different formulations of TLC (TLC alone, anionic liposomes with TLC and cationic liposomes with TLC).

As evidenced in FIG. 13a, there was a considerable distinction across the dose dependent range of immune response in aggregate levels of anti-tetanus antibody IgG raised between the anionic and cationic variants of the lipid adjuvants used in both studies. Specifically, the cationic liposomes, whether liquid or freeze-dried, raised at least five times the antibody levels when compared with the anionic liposomes.

Figure 13B:
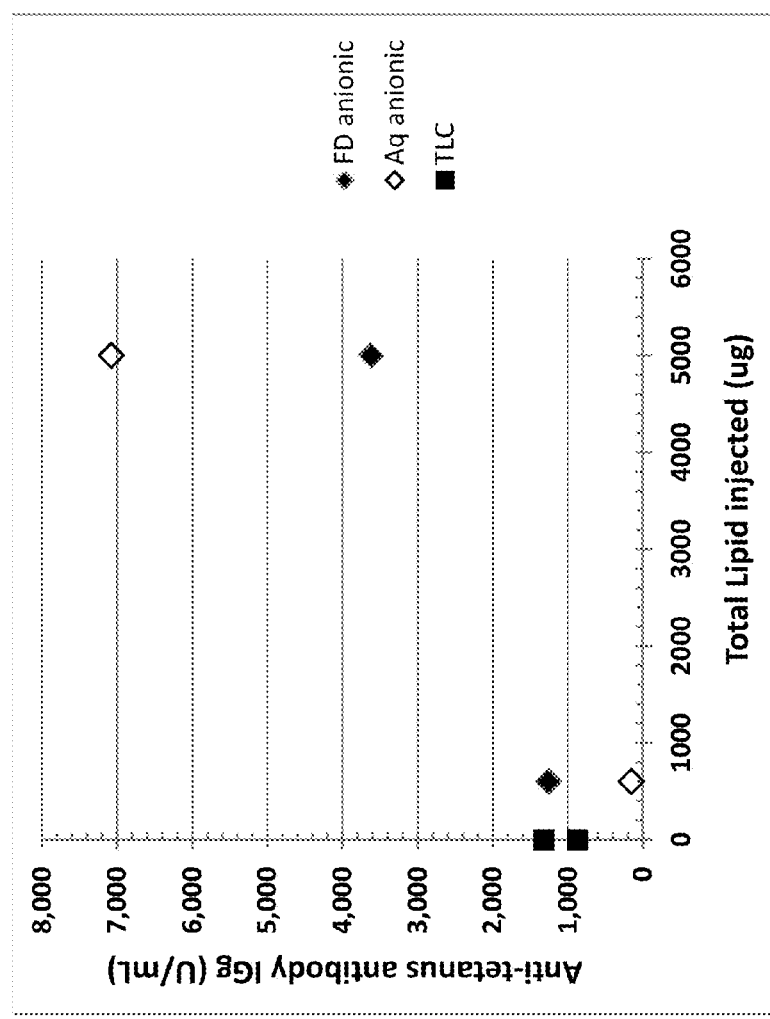
FIG. 13b indicates the dose dependence of immune response for anionic liposomes as compared to TLC only. The anionic liposome formulations at higher lipid content were prepared at pH 4, whereas those at lower lipid content were prepared at pH 7.

A deeper analysis of the data from the dose dependent ranges of immune response across all TLC formulations found a benefit of anionic liposomes as compared to TLC alone (FIG. 13b). The anionic liposome formulations were prepared at two different pH concentrations, depending on lipid content (higher lipid content formulations were prepared at pH 4 and lower lipid content formulations were prepared at pH 7).

Figure 14A:
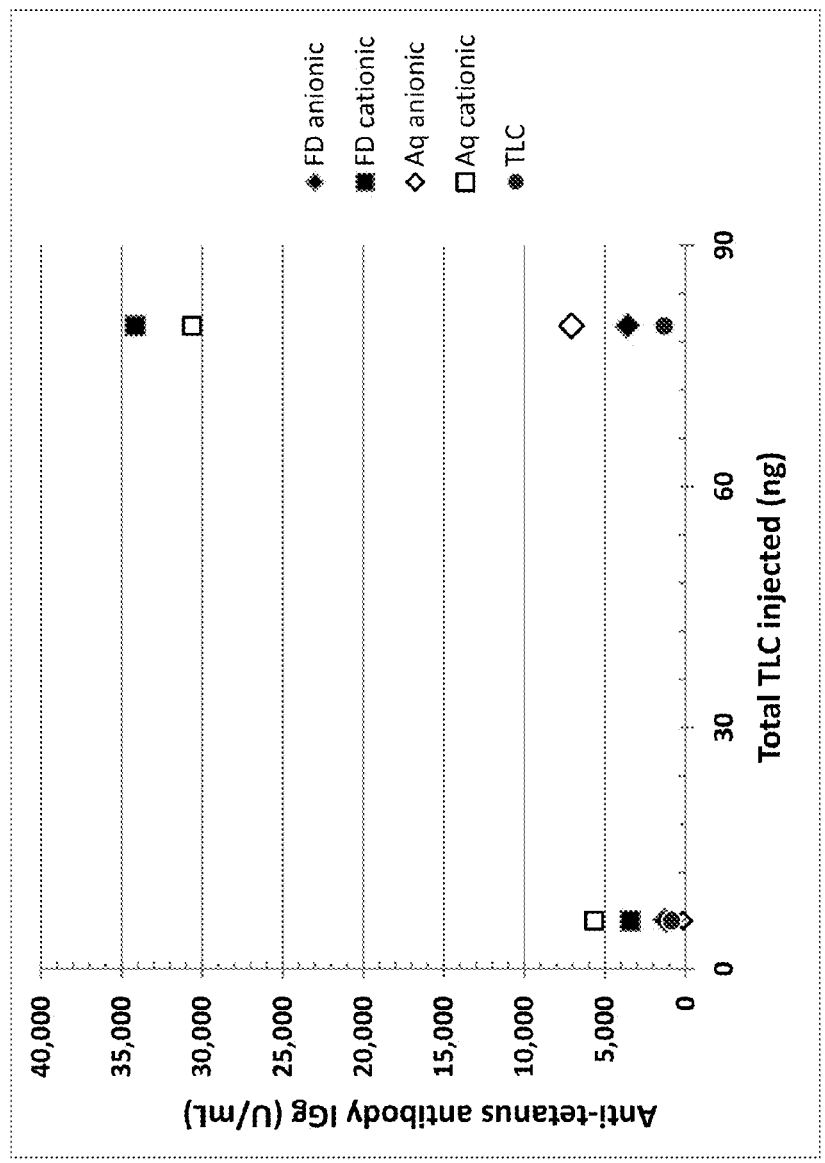
FIG. 14a shows a comparison of the immunogenicity in mice of different formulations as a function of TLC concentration.
Figure 14B:
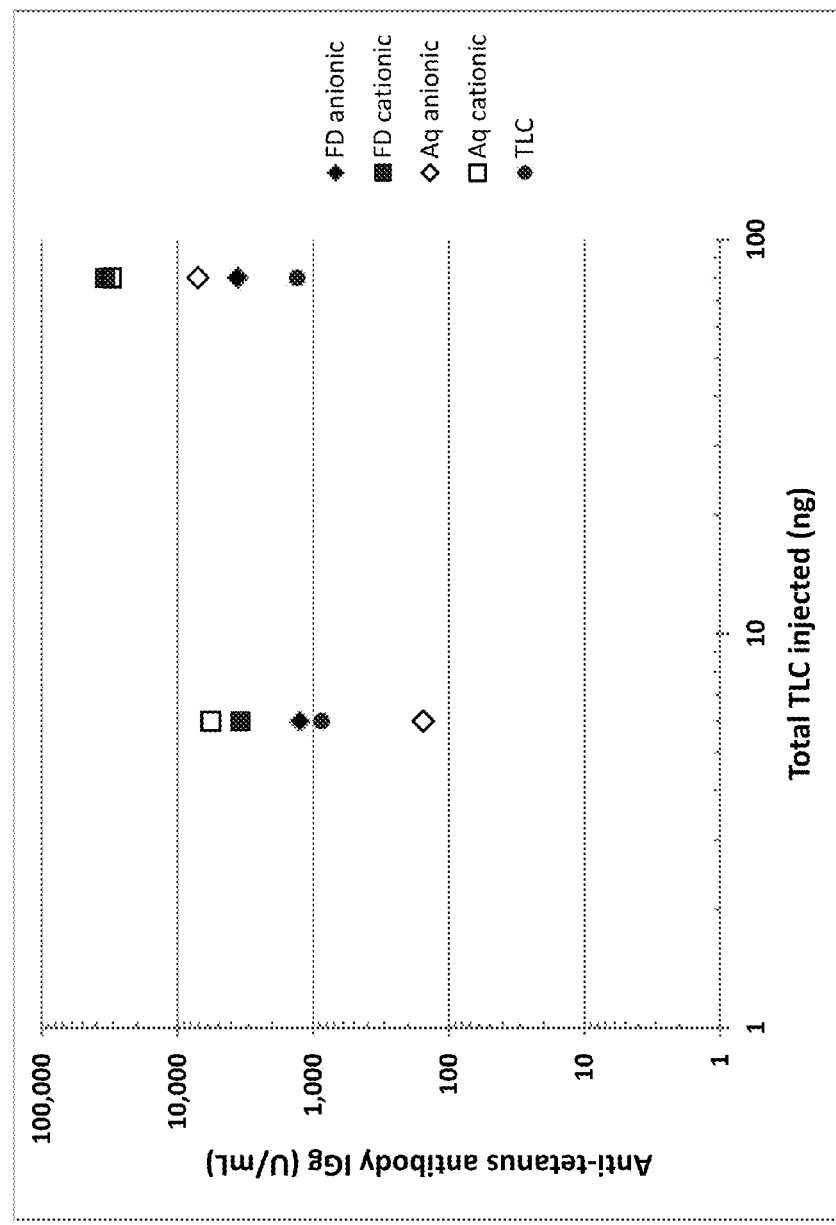
FIG. 14b indicates a similar comparison across the immunogenicity levels in mice of different formulations as a function of TLC concentration on a logarithmic scale.
Figure 15A:
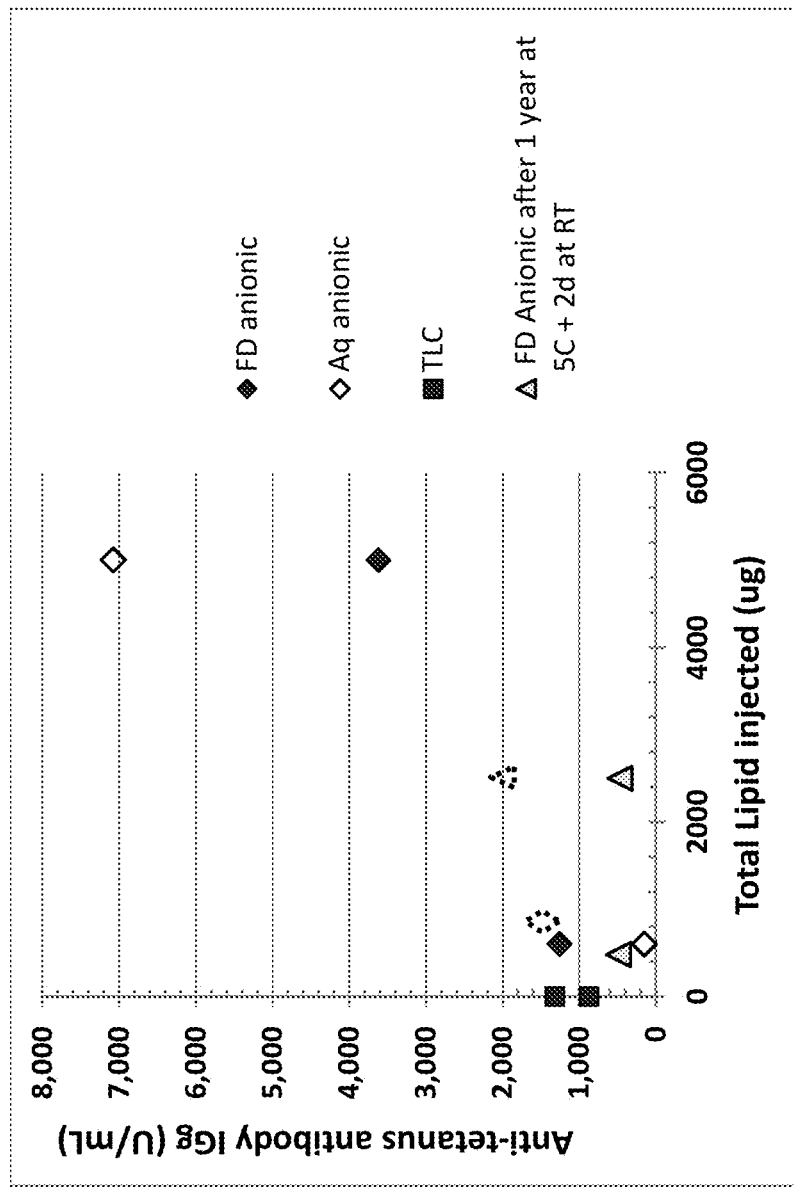
FIG. 15a shows comparison between anionic lipid compositions after 2 shots and 28 days after the 1$^{st}$ shot, except results for freeze-dried anionic liposomes (yellow symbols) which are based on 1 shot and 14 days after the shot. The dashed symbols are expected values after 28 days read from the linear regression lines from the actual values after 28 days and 2 shots.
Figure 15B:
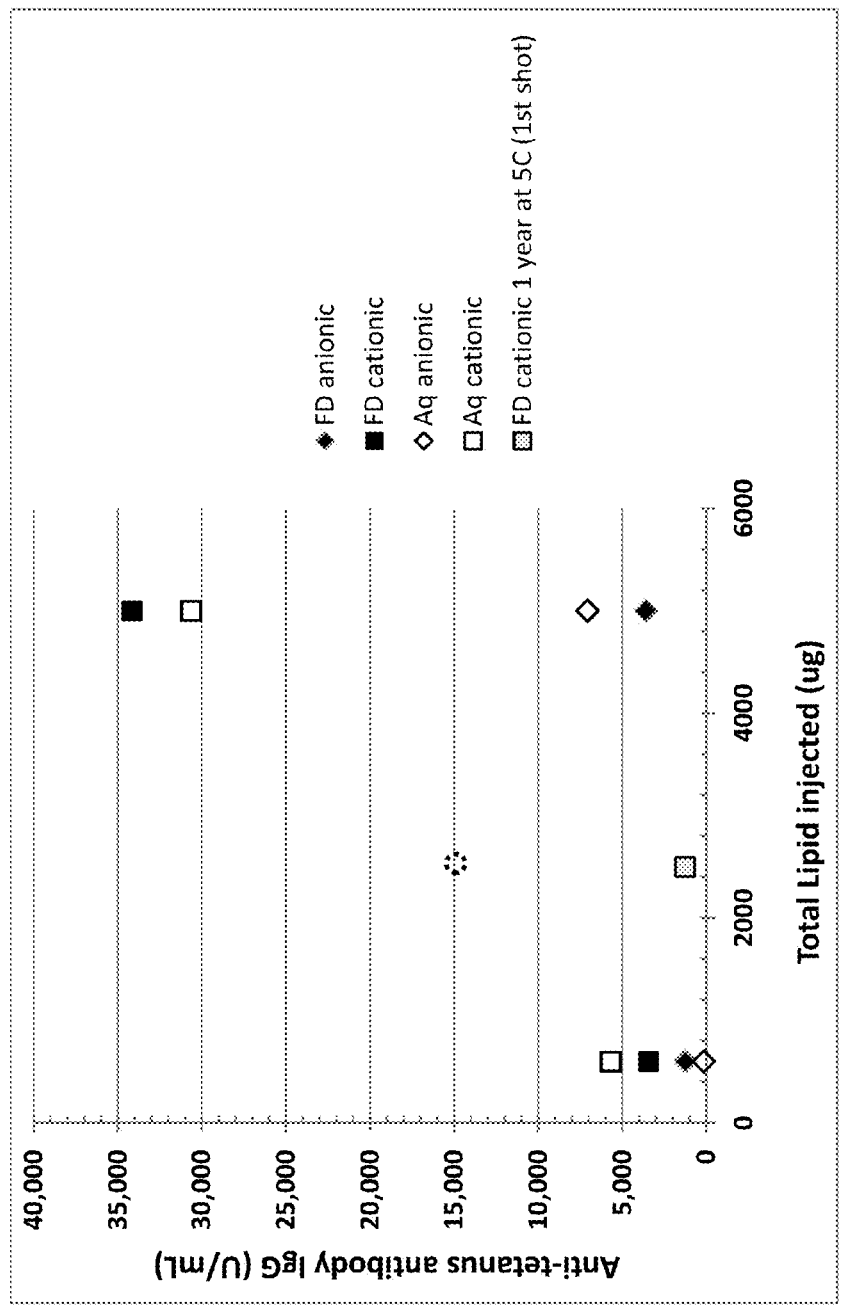
FIG. 15b presents the additional cationic lipid composition data points.

Additional examination of comparisons of the immunogenicity in mice of different formulations as a function of TLC concentration was also undertaken (FIG. 14a). Specifically, when analyzing immunogenicity as a function of total TLC injected (ng), the data consistently indicates the benefit of the cationic formulations (both liquid and freeze-dried) when compared with the anionic formulations. Such benefit remains even when the data are viewed in a log scale format (FIG. 14b), indicating the remarkable improvement attained with respect to immunogenicity when altering the charged lipid in the liposomal vaccine adjuvant from DPPG (anionic) to SA (cationic). This additionally would enable the development of vaccine requiring a lower dose of TLC, therefore reducing costs as well as potential negative reactions to an individual's immune system.

V. Stability Analysis from Studies

Lyophilized liposomal tetanus vaccines (SP-318-3, SP-318-5, SP-329-3 and SP-329-5) were stored at 5° C.±2° C. for about 1 year. At the end of this time they were also stored at room temperature (22° C.±2° C.) for 2 days and then tested in mice for immunogenicity. In these studies the dose was increased from 50 µl to 80 µl for anionic liposomes with 0.1 µg/ml TLC (SP-318-3 and SP-318-5 from Tetanus study 1).

Since the lyophilized liposomal vaccine vials from Study 2 of tetanus were limited, the mice received only 1 dose in the groups receiving anionic and cationic liposomes containing 0.4 µg/ml TLC and 2.5 mg/ml adjuvant (lipid) (SP-329-3 and SP-329-5). The sera of mice were analyzed 2 weeks after the 1st dose by ELISA (as previously detailed) and at the end of study, i.e. 28 days after the 1st dose.

1 Year Stability Study of TLC Liposomes at 2-8° C.

The IgG response against tetanus toxoid in mice obtained after the first shot, 14 days after the shot, showed that in average for both anionic liposomes (SP-318-3 and SP-329-3), similar IgG response was obtained in mice (490+76 U/ml and 470+48, respectively). This showed that increase of the amount of TLC injected from 10 ng to 40 ng in each case, or increase in the amount of adjuvant (lipid) injected from 0.48 mg to 2.5 mg in each case, did not have any effect on the immune response obtained in mice after such a short time as 14 days after the 1st shot. Similar results were obtained for cationic liposomes at lower dose of TLC (10 ng) and lipid (0.48 mg), i.e 445+76 U/ml.

However, the cationic liposomes at higher dose (40 ng TLC and 2.5 mg lipid) gave a higher immune response (1,268+237 U/ml), 14 days after the 1st shot was received by mice, as detailed and compared with specific stability elements from each composition (Table 14).

TABLE 14

Stability Results for Cationic and Anionic Lyophilized Liposomes Associated with TLC

| ID | Antigen | Booster shot | TLC (ug/mL) | TLC/inj (ng) | Vol. inj/time point (ul) | Lipid (ug/mL) | Total lipid Conc after 1st shot (ug) | Ratio (Lipid/TLC) (ug/ug) | Immune response (14 days after 1st shot) | Immune response (28 days after 1st shot or 14 days after 2nd shot) |
|---|---|---|---|---|---|---|---|---|---|---|
| SP-318-3[a] (1 Year at 5° C.) | TLC | Y | 0.12 | 10 | 80 | 6000 | 480 | 50,000 | 490 ± 76 | TBD (expecting 1,300)[e] |
| SP-318-5[b] (1 Year at 5° C.) | TLC | Y | 0.12 | 10 | 80 | 6000 | 480 | 50,000 | 445 ± 76 | TBD (expecting 4,000)[e] |
| SP-329-3[c] (1 Year at 5° C.) | TLC | N | 0.40 | 40 | 100 | 25,000 | 2,500 | 62,500 | 470 ± 48 | TBD (expecting 2,000)[e] |
| SP-329-5[d] (1 Year at 5° C.) | TLC | N | 0.40 | 40 | 100 | 25,000 | 2,500 | 62,500 | 1,268 ± 237 | TBD (expecting 6,000)[e] |

[a]SP-318-3 is the anionic liposomal vaccine with 0.12 μg/ml TLC and 6,000 μg/ml lipid
[b]SP-318-5 is the cationic liposomal vaccine with 0.12 μg/ml TLC and 6,000 μg/ml lipid
[c]SP-329-3 is the anionic liposomal vaccine with 0.40 μg/ml TLC and 25,000 μg/ml lipid
[d]SP-329-5 is the cationic liposomal vaccine with 0.12 μg/ml TLC and 25,000 μg/ml lipid Immunogenicity was also assessed (FIG. 15a-b) as compared across lipid charge (anionic versus cationic) and time after first shot. Final prophetic amounts are plotted based on expected values after 28 days as read from linear regression lines from actual values attained after 28 days and 2 shots.

It is also clear that all liposomal vaccines described in the present invention provide a better immune response, with sustained greater immunogenicity, and a lower antigen dose, as compared to TLC adsorbed to the Adju-Phos®-like systems of the prior art.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. An injectable immunogenic composition comprised of a liposome-associated antigen, wherein said liposome comprises: dipalmitoyl phosphatidylcholine (DPPC), dioleoyl phosphatidylcholine (DOPC), cholesterol and stearylamine (SA) wherein said antigen is entrapped within the aqueous compartment of said liposome, entrapped within the lipid bilayer, and/or adsorbed to the liposomal surface wherein the DPPC:DOPC:cholesterol:positively charged lipid molar ratio is 40:20-30:20:10-20; wherein said antigen is at least one member selected from the group consisting of polynucleotides, polypeptides, recombinant proteins, synthetic peptides and protein extract isolated from pathogens selected from the group consisting *Corynebacterium diphtheria, Bordetella pertussis*, influenza virus, hepatitis B virus, *Clostridium botulinum* and *Bacillus anthracis* and further wherein the composition includes lysozyme.

2. The immunogenic composition of claim 1, wherein the injectable, liposomal vaccine is formulated as a lyophilized composition.

3. The immunogenic composition of claim 1, further wherein the liposomes maintain a mean hydrodynamic particle diameter of between about 300 nm to about 1000 nm.

4. The immunogenic composition of claim 1, wherein the liposomal vaccine maintains immunogenicity after lyophilization and in the presence of at least one lyoprotectant.

5. The immunogenic composition of claim 4, wherein the at least one lyoprotectant is selected from the group consisting of sucrose, trehalose and mannitol.

6. The immunogenic composition of claim 1, wherein the liposomal composition is stable after storage at sub-zero temperatures and room temperatures for a period of time greater than six months.

7. The immunogenic composition of claim 1, wherein the vaccine is formulated in the absence of a co-adjuvant.

\* \* \* \* \*